US008362278B2

(12) United States Patent
Kreischer et al.

(10) Patent No.: US 8,362,278 B2
(45) Date of Patent: Jan. 29, 2013

(54) METHODS FOR THE CONVERSION OF A SUBSTITUTED FURAN TO A SUBSTITUTED PYRROLE

(75) Inventors: Bruce E. Kreischer, Kingwood, TX (US); Orson L. Sydora, Houston, TX (US); Steven Hutchinson, Spring, TX (US); Eduardo J. Baralt, Kingwood, TX (US); Ron D. Knudsen, Bartlesville, OK (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 30 days.

(21) Appl. No.: 12/895,945

(22) Filed: Oct. 1, 2010

(65) Prior Publication Data

US 2012/0083609 A1 Apr. 5, 2012

(51) Int. Cl.
*C07D 207/323* (2006.01)
(52) U.S. Cl. ........................................ 548/564; 548/560
(58) Field of Classification Search .................. None
See application file for complete search history.

(56) References Cited

U.S. PATENT DOCUMENTS

| | | | |
|---|---|---|---|
| 2,600,289 A | 6/1952 | Bordner | |
| 3,900,479 A * | 8/1975 | Massie | 546/191 |
| 4,060,480 A | 11/1977 | Reed et al. | |
| 4,452,910 A | 6/1984 | Hopkins et al. | |
| 5,376,611 A | 12/1994 | Shveima | |
| 6,107,230 A | 8/2000 | McDaniel et al. | |
| 6,165,929 A | 12/2000 | McDaniel et al. | |
| 6,294,494 B1 | 9/2001 | McDaniel et al. | |
| 6,300,271 B1 | 10/2001 | McDaniel et al. | |
| 6,316,553 B1 | 11/2001 | McDaniel et al. | |
| 6,355,594 B1 | 3/2002 | McDaniel et al. | |
| 6,376,415 B1 | 4/2002 | McDaniel et al. | |
| 6,388,017 B1 | 5/2002 | McDaniel et al. | |
| 6,391,816 B1 | 5/2002 | McDaniel et al. | |
| 6,395,666 B1 | 5/2002 | McDaniel et al. | |
| 6,524,987 B1 | 2/2003 | Collins et al. | |
| 6,548,441 B1 | 4/2003 | McDaniel et al. | |
| 6,548,442 B1 | 4/2003 | Collins et al. | |
| 6,576,583 B1 | 6/2003 | McDaniel et al. | |
| 6,613,712 B1 | 9/2003 | McDaniel et al. | |
| 6,632,894 B1 | 10/2003 | McDaniel et al. | |
| 6,667,274 B1 | 12/2003 | Hawley et al. | |
| 6,750,302 B1 | 6/2004 | McDaniel et al. | |
| 7,176,159 B1 | 2/2007 | Wheelock et al. | |
| 7,572,925 B2 | 8/2009 | Dumesic et al. | |
| 7,618,612 B2 | 11/2009 | Cortright et al. | |
| 7,671,246 B2 | 3/2010 | Dumesic et al. | |
| 2007/0129243 A1 | 6/2007 | Wheelock et al. | |
| 2007/0225383 A1 | 9/2007 | Cortright et al. | |
| 2009/0124839 A1 | 5/2009 | Dumesic et al. | |
| 2009/0255171 A1 | 10/2009 | Dumesic et al. | |
| 2010/0076167 A1 | 3/2010 | McDaniel et al. | |

FOREIGN PATENT DOCUMENTS

JP 2002-193390 * 7/2002

OTHER PUBLICATIONS

Jia, Meng-qui et al., "Heterogenous Catalysts for the Synthesis of Pyrrole from Furan and Ammonia", Journal of Beijing University of Chemical Technology, vol. 33, No. 3, 98-102, 2006.*
Yur'ev et al., Chemical Abstracts, 37:25236, 1943.*
Yur'ev et al., Chemical Abstracts, 47:15841, 1953.*
Cooney et al., Fuel, 65(3), 433-436, Mar. 1986.*
Elming et al., Acta Chemica Scandinavica, 6, 867-874, 1952.*
Sheldon, R.A. et al., "Heterogeneous Catalytic Transformations for Environmentally Friendly Production", Applied Catalysis A: General 189, 163-183, 1999.*
Banik, Bimal K. et al., "Simple Synthesis of Substituted Pyrroles", Journal of Organic Chemistry, 69(1), 213-216, 2004.*
Iovel, I.G. et al., "Hydroxymethylation and Alkylation of Compounds of the Furan, Thiophene, and Pyrrole Series in the Presence of H+ Cations (Review)", Chemistry of Heterocyclic Compounds, 34(1), 1-12, 1998.*
Pitmann, Charles U. et al., "Sequential Catalytic Condensation-Hydrogenation of Ketones", Journal of Organic Chemistry, 45, 5048-5052, 1980.*
Ranu, Brindaban C. et al., "Zinc Tetrafluoroborate-Catalysed Synthesis of Highly Substituted Pyrroles by a Solvent-Free Reaction", Mendeleev Communications, 16(4), 220-221, 2006.*
Yang, Tien-syh et al., "Acidities of sulfate species formed on a superacid of sulfated alumina", Journal of Molecular Catalysis A: Chemical 115, 339-346, 1997.*
Chemical Abstracts, 137:63172, 2002. (Chemical Abstract of Japanese Patent 2002-193930, Jul. 20, 2002).*
Yuan, Shizhen et al., "A Simple Synthesis of Pyrroles Catalyzed by Acidic Resin under Solvent-Free Condition", Journal of Heterocyclic Chemistry 47(2), 446-448, published online Feb. 23, 2010.*
Machine Translation of JP 2002-193930, downloaded Jul. 12, 2011.*
English translation of Jia, Meng-qui et al., "Heterogenous Catalysts for the Synthesis of Pyrrole from Furan and Ammonia", Journal of Beijing University of Chemical Technology, vol. 33, No. 3, 98-102, 2006.*
Albrecht et al., "Application of a Combined Catalyst and Sorbent for Steam Reforming of Methane," Ind. Eng. Chem. Res., 2010, 49, pp. 4091-4098.
Amarnath et al., "Intermediates in the Paal-Knorr Synthesis of Pyrroles," J. Org. Chem., 1991, 56, pp. 6924-6931.
Amarnath et al., "Intermediates in the Paal-Knorr Synthesis of Furans," J. Org. Chem., 1995, 60, pp. 301-307.
Barrer, "Hydrothermal Chemistry of Zeolites: Some Properties of Zeolites," Academic Press (Department of Chemistry Imperial College of Science and Technology London), 1982, 25 pages.
Davis, "Zeolites and Molecular Sieves: Not Just Ordinary Catalysts," Ind. Eng. Chem. Res., 1991, 30, pp. 1675-1683.
Davis et al., "Zeolite and Molecular Sieve Synthesis," Chem. Mater., 1992, 4, pp. 756-768.
Roman-Leshkov et al., "Production of dimethylfuran for liquid fuels from biomass-derived carbohydrates," Nature, 2007, vol. 447, 4 pages.
Hakim, "A Comparative Study of Macroporous Metal Oxides Synthesized via a Unified Approach," Chem. Mater., 2009, 21, pp. 2027-2038.

(Continued)

*Primary Examiner* — Fiona T Powers
(74) *Attorney, Agent, or Firm* — Merchant & Gould P.C.

(57) ABSTRACT

The present invention discloses processes for producing substituted pyrrole compounds, such as 2,5-disubstituted pyrroles. Synthetic processes which directly convert substituted furan compounds to substituted pyrrole compounds, via a reaction of the substituted furan compound with ammonia and/or an ammonium salt in the presence of a catalyst, also are described.

23 Claims, No Drawings

OTHER PUBLICATIONS

Hatada et al., "Ring transformations of oxygen containing heterocycles into nitrogen containing heterocycles over synthetic zeolites," Chemistry Letters, 1974, pp. 439-442.

Heterocyclic Chemistry, "Heterocyclic Compounds," http://www2.chemistry.msu.edu/faculty/reusch/VirtTxtJml/heterocy.htm, 2010, pp. 1-16.

Hruby et al., "Acid-base cooperativity in condensation reactions with functionalized mesoporous silica catalysts," J. Cat., 2009, 263, pp. 181-188.

Ma et al., "A review of zeolite-like porous materials," Microporous and Mesoporous Materials, 2000, 37, pp. 243-252.

Miao et al., "Esterification of biomass pyrolysis model acides over sulfonic acid-functionalized mesoporous silicas," Appl. Catal. A: Gen. 2009, 359, pp. 113-120.

Meier et al., "Atlas of Zeolite Structure Types," Structure Commission of the International Zeolite Association, Butterworth & Co., 1987, 16 pages.

Pinnavaia, "Intercalated Clay Catalysts," Science, 1983, vol. 220, No. 4595, pp. 365-371.

Serrano-Ruiz, "Catalytic Conversion of Renewable Biomass Resources to Fuels and Chemicals," Annu. Rev. Chem. Biomol. Eng., 2010, 1:79-100, 26 pages.

Snell et. al., "Aldol Condensations Using Bio-oil Model Compounds: The Role of Acid-Base Bi-functionality," Top. Catal., 2010, vol. 53, pp. 1248-1253.

Thomas, "Sheet Silicate Intercalates: New Agents for Unusual Chemical Conversions," Intercalation Chemistry, 1982, ISBN 0-12-747380-7, pp. 55-99.

Young et al., "2,5-Dimethylpyrrole [Pyrrole, 2,5-dimethyl-]," Organic Syntheses, Coll., 1943, vol. 2, p. 219; 1936, vol. 16, p. 25.

Hawley's Condensed Chemical Dictionary, $11^{th}$ Ed., John Wiley & Sons, 1995, 3 pages.

Cotton et al., Advanced Inorganic Chemistry, $6^{th}$ Ed., Wiley-Interscience, 1999, 4 pages.

* cited by examiner

US 8,362,278 B2

METHODS FOR THE CONVERSION OF A SUBSTITUTED FURAN TO A SUBSTITUTED PYRROLE

BACKGROUND OF THE INVENTION

The present invention relates generally to processes for producing substituted pyrrole compounds. Certain substituted pyrrole compounds—for example, 2,5-dimethylpyrrole—can be used as a component in an oligomerization catalyst system to produce an α-olefin oligomer, such as 1-hexene or 1-octene, from ethylene.

Processes to produce substituted pyrroles from substituted furans generally involve two distinct steps. For example, the first step can involve a ring-opening reaction of the substituted furan to form a dione. The second step can involve a ring-forming reaction of the dione to produce the substituted pyrrole. It would be beneficial to develop new synthetic methods to produce substituted pyrroles from substituted furans. Accordingly, it is to this end that the present invention is directed.

SUMMARY OF THE INVENTION

Processes for producing substituted pyrrole compounds are disclosed herein. In accordance with embodiments of the present invention, one such process comprises:
1) contacting
   a) a substituted furan compound;
   b) ammonia, an ammonium salt, or a combination thereof; and
   c) a catalyst; and
2) forming the substituted pyrrole compound.

In some embodiments, the disclosed processes can be used to produce 2,5-disubstituted pyrroles (e.g., 2,5-dimethylpyrrole).

Definitions

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, $2^{nd}$ Ed (1997) can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Regarding claim transitional terms or phrases, the transitional term "comprising," which is synonymous with "including," "containing," "having," or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps and those that do not materially affect the basic and novel characteristic(s) of the claimed invention. A "consisting essentially of" claim occupies a middle ground between closed claims that are written in a "consisting of" format and fully open claims that are drafted in a "comprising" format. Absent an indication to the contrary, describing a compound or composition as "consisting essentially of" is not to be construed as "comprising," but is intended to describe the recited component that includes materials which do not significantly alter the composition or method to which the term is applied. For example, a feedstock consisting essentially of a material A can include impurities typically present in a commercially produced or commercially available sample of the recited compound or composition. When a claim includes different features and/or feature classes (for example, a method step, feedstock features, and/or product features, among other possibilities), the transitional terms comprising, consisting essentially of, and consisting of apply only to the feature class to which it is utilized, and it is possible to have different transitional terms or phrases utilized with different features within a claim. For example, a method can comprise several recited steps (and other non-recited steps), but utilize a system preparation consisting of specific components; alternatively, consisting essentially of specific components; or alternatively, comprising the specific components and other non-recited components.

While compositions and methods are described in terms of "comprising" various components or steps, the compositions and methods can also "consist essentially of" or "consist of" the various components or steps, unless stated otherwise.

The terms "a," "an," and "the" are intended to include plural alternatives, e.g., at least one. For instance, the disclosure of "a substituted furan compound," "an ammonium salt," etc., is meant to encompass one, or mixtures or combinations of more than one, substituted furan compound, ammonium salt, etc., unless otherwise specified.

Unless otherwise specified, the use of "ppm" refers to parts per million by weight.

For any particular compound or group disclosed herein, any name or structure presented is intended to encompass all conformational isomers, regioisomers, stereoisomers, and mixtures thereof that may arise from a particular set of substituents, unless otherwise specified. The name or structure also encompasses all enantiomers, diastereomers, and other optical isomers (if there are any) whether in enantiomeric or racemic forms, as well as mixtures of stereoisomers, as would be recognized by a skilled artisan, unless otherwise specified. For example, a general reference to pentane includes n-pentane, 2-methyl-butane, and 2,2-dimethylpropane; and a general reference to a butyl group includes a n-butyl group, a sec-butyl group, an iso-butyl group, and a t-butyl group.

Within this disclosure, the normal rules of organic nomenclature will prevail. For instance, when referencing substituted compounds or groups, references to substitution patterns are taken to indicate that the indicated group(s) is(are) located at the indicated position and that all other non-indicated positions are hydrogen. For example, reference to a 4-substituted phenyl group indicates that there is a non-hydrogen substituent located at the 4 position and hydrogens located at the 2, 3, 5, and 6 positions. By way of another example, reference to a 3-substituted naphth-2-yl indicates that there is a non-hydrogen substituent located at the 3 position and hydrogens located at the 1, 4, 5, 6, 7, and 8 positions. References to compounds or groups having substitutions at positions in addition to the indicated position will be referenced using comprising or some other alternative language. For example, a reference to a phenyl group comprising a substituent at the 4 position refers to a phenyl group having a substituent at the 4 position and hydrogen or any non-hydrogen substituent at the 2, 3, 5, and 6 positions.

In one embodiment, a chemical "group" can be defined or described according to how that group is formally derived from a reference or "parent" compound, for example, by the number of hydrogen atoms removed from the parent compound to generate the group, even if that group is not literally synthesized in such a manner. These groups can be utilized as substituents or coordinated or bonded to metal atoms. By way of example, an "alkyl group" formally can be derived by removing one hydrogen atom from an alkane, while an "alkylene group" formally can be derived by removing two hydrogen atoms from an alkane. Moreover, a more general term can be used to encompass a variety of groups that formally are derived by removing any number ("one or more") hydrogen atoms from a parent compound, which in this example can be described as an "alkane group," and which encompasses an "alkyl group," an "alkylene group," and materials having three or more hydrogen atoms, as necessary for the situation, removed from an alkane. The disclosure that a substituent, ligand, or other chemical moiety may constitute a particular "group" implies that the well-known rules of chemical structure and bonding are followed when that group is employed as described. When describing a group as being "derived by," "derived from," "formed by," or "formed from," such terms are used in a formal sense and are not intended to reflect any specific synthetic methods or procedures, unless specified otherwise or the context requires otherwise.

Also, unless otherwise specified, any carbon-containing group for which the number of carbon atoms is not specified can have, according to proper chemical practice, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 carbon atoms, or any range or combination of ranges between these values. For example, unless otherwise specified, any carbon-containing group can have from 1 to 30 carbon atoms, from 1 to 25 carbon atoms, from 1 to 20 carbon atoms, from 1 to 15 carbon atoms, from 1 to 10 carbon atoms, or from 1 to 5 carbon atoms, and the like. Moreover, other identifiers or qualifying terms may be utilized to indicate the presence of, or absence of, a particular substituent, a particular regiochemistry, and/or stereochemistry, or the presence of absence of a branched underlying structure or backbone. Any specific carbon-containing group is limited according to the chemical and structural requirements for that specific group, as understood by one of ordinary skill. For example, unless otherwise specified, an aryl group can have from 6 to 30 carbon atoms, from 6 to 25 carbon atoms, from 6 to 20 carbon atoms, from 6 to 15 carbon atoms, or from 6 to 10 carbon atoms, and the like. Thus, according to proper chemical practice and unless otherwise specified, an aryl group can have 6, 7, 8, 9, 10, 11, 12, 13, 14, 15, 16, 17, 18, 19, 20, 21, 22, 23, 24, 25, 26, 27, 28, 29, or 30 carbon atoms, or any range or combination of ranges between these values.

Other numerical ranges are disclosed herein. When Applicants disclose or claim a range of any type, Applicants' intent is to disclose or claim individually each possible number that such a range could reasonably encompass, including end points of the range as well as any sub-ranges and combinations of sub-ranges encompassed therein, unless otherwise specified. As a representative example, Applicants disclose that a weight ratio of a substituted pyrrole compound to reaction by-products can be in a range from 0.5:1 to 10:1, in an embodiment of the invention. By a disclosure that the weight ratio of the substituted pyrrole compound to reaction by-products can be in a range from 0.5:1 to 10:1, Applicants intend to recite that the molar ratio can be 0.5:1, about 0.6:1, about 0.7:1, about 0.8:1, about 0.9:1, about 1:1, about 1.5:1, about 2:1, about 2.5:1, about 3:1, about 3.5:1, about 4:1, about 4.5:1, about 5:1, about 5.5:1, about 6:1, about 6.5:1, about 7:1, about 7.5:1 about 8:1, about 8.5:1 about 9:1, about 9.5:1, or 10:1. Additionally, the weight ratio can be within any range from 0.5:1 to 10:1 (for example, the weight ratio is in a range from about 2:1 to about 8:1), and this also includes any combination of ranges between 0.5:1 and 10:1. Likewise, all other ranges disclosed herein should be interpreted in a manner similar to these examples.

Applicants reserve the right to proviso out or exclude any individual members of any such group, including any sub-ranges or combinations of sub-ranges within the group, that can be claimed according to a range or in any similar manner, if for any reason Applicants choose to claim less than the full measure of the disclosure, for example, to account for a reference that Applicants may be unaware of at the time of the filing of the application. Further, Applicants reserve the right to proviso out or exclude any individual substituents, analogs, compounds, ligands, structures, or groups thereof, or any members of a claimed group, if for any reason Applicants choose to claim less than the full measure of the disclosure, for example, to account for a reference that Applicants may be unaware of at the time of the filing of the application.

The term "substituted" when used to describe a group, for example, when referring to a substituted analog of a particular group, is intended to describe the compound or group wherein any non-hydrogen moiety formally replaces hydrogen in that group or compound, and is intended to be non-limiting. A compound or group may also be referred to herein as "unsubstituted" or by equivalent terms such as "non-substituted," which refers to the original group or compound. "Substituted" is intended to be non-limiting and include inorganic substituents or organic substituents as specified and as understood by one of ordinary skill in the art.

A "halide" has its usual meaning. Examples of halides include fluoride, chloride, bromide, and iodide.

The term "organyl group" is used herein in accordance with the definition specified by IUPAC: an organic substituent group, regardless of functional type, having one free valence at a carbon atom. Similarly, an "organylene group" refers to an organic group, regardless of functional type, derived by removing two hydrogen atoms from an organic compound (either two hydrogen atoms from one carbon atom or one hydrogen atom from each of two different carbon atoms). An "organic group" refers to a generalized group formed by removing one or more hydrogen atoms from carbon atoms of an organic compound. Thus, an "organyl group," an "organylene group," and an "organic group" can contain organic functional group(s) and/or atom(s) other than carbon and hydrogen, that is, an organic group that can comprise functional groups and/or atoms in addition to carbon and hydrogen. For instance, non-limiting examples of atoms other than carbon and hydrogen include halogens, oxygen, nitrogen, phosphorus, and the like. Non-limiting examples of functional groups include ethers, aldehydes, ketones, esters, sulfides, amines, and phosphines, and so forth. In one embodiment, the hydrogen atom(s) removed to form the "organyl group," "organylene group," or "organic group" may be attached to a carbon atom belonging to a functional group, for example, an acyl group (—C(O)R), a formyl group (—C(O)H), a carboxy group (—C(O)OH), a hydrocarboxycarbonyl group (—C(O)OR), a cyano group (—CN), a carbamoyl group (—C(O)NH$_2$), a N-hydrocarbylcarbamoyl group (—C(O)NHR), or N,N'-dihydrocarbylcarbamoyl group (—C(O)NR$_2$), among other possibilities. In another embodiment, the hydrogen atom(s) removed to form the "organyl group," "organylene group," or "organic group" may be attached to a carbon atom not belonging to, and remote from, a functional group, for example, —CH$_2$C(O)CH$_3$, —CH$_2$N(CH$_3$)$_2$, and the like. An "organyl group," "organylene group," or "organic group" may be aliphatic or aromatic, cyclic or acyclic, and/or linear or branched. "Organyl groups," "organylene groups,"

and "organic groups" also encompass heteroatom-containing rings, heteroatom-containing ring systems, heteroaromatic rings, and heteroaromatic ring systems. Finally, it is noted that the "organyl group," "organylene group," or "organic group" definitions include "hydrocarbyl group," "hydrocarbylene group," "hydrocarbon group," respectively, and "alkyl group," "alkylene group," and "alkane group," respectively, among others, as members.

The term "hydrocarbon" whenever used in this specification and claims refers to a compound containing only carbon and hydrogen. Other identifiers may be utilized to indicate the presence of particular groups in the hydrocarbon (e.g. halogenated hydrocarbon indicates that the presence of one or more halogen atoms replacing an equivalent number of hydrogen atoms in the hydrocarbon). The term "hydrocarbyl group" is used herein in accordance with the definition specified by IUPAC: a univalent group formed by removing a hydrogen atom from a hydrocarbon (that is, a group containing only carbon and hydrogen). Similarly, a "hydrocarbylene group" refers to a group formed by removing two hydrogen atoms from a hydrocarbon, either two hydrogen atoms from one carbon atom or one hydrogen atom from each of two different carbon atoms. Therefore, in accordance with the terminology used herein, a "hydrocarbon group" refers to a generalized group formed by removing one or more hydrogen atoms (as needed for the particular group) from a hydrocarbon. A "hydrocarbyl group," "hydrocarbylene group," and "hydrocarbon group" can be acyclic or cyclic groups, and/or may be linear or branched. A "hydrocarbyl group," "hydrocarbylene group," and "hydrocarbon group" can include rings, ring systems, aromatic rings, and aromatic ring systems, which contain only carbon and hydrogen. "Hydrocarbyl groups," "hydrocarbylene groups," and "hydrocarbon groups" include, by way of example, aryl, arylene, arene groups, alkyl, alkylene, alkane group, cycloalkyl, cycloalkylene, cycloalkane groups, aralkyl, aralkylene, and aralkane groups, respectively, among other groups as members.

An aliphatic compound is a non-aromatic organic compound. An "aliphatic group" is a generalized group formed by removing one or more hydrogen atoms (as needed for the particular group) from the carbon atoms of an aliphatic compound. An aliphatic compound may be acyclic or cyclic, saturated or unsaturated, and/or linear or branched organic compound. Aliphatic compounds and aliphatic groups may contain organic functional group(s) and/or atom(s) other than carbon and hydrogen unless otherwise specified (e.g., aliphatic hydrocarbon).

The term "alkane" whenever used in this specification and claims refers to a saturated hydrocarbon compound. Other identifiers may be utilized to indicate the presence of particular groups in the alkane (e.g. halogenated alkane indicates that the presence of one or more halogen atoms replacing an equivalent number of hydrogen atoms in the alkane). The term "alkyl group" is used herein in accordance with the definition specified by IUPAC: a univalent group formed by removing a hydrogen atom from an alkane. Similarly, an "alkylene group" refers to a group formed by removing two hydrogen atoms from an alkane (either two hydrogen atoms from one carbon atom or one hydrogen atom from two different carbon atoms). An "alkane group" is a general term that refers to a group formed by removing one or more hydrogen atoms (as needed for the particular group) from an alkane. An "alkyl group," "alkylene group," and "alkane group" may be linear or branched unless otherwise specified. Primary, secondary, and tertiary alkyl groups are derived by removal of a hydrogen atom from a primary, secondary, tertiary carbon atom, respectively, of an alkane. The n-alkyl group is derived by removal of a hydrogen atom from a terminal carbon atom of a linear alkane. The groups $RCH_2$ ($R \neq H$), $R_2CH(R \neq H)$, and $R_3C(R \neq H)$ are primary, secondary, and tertiary alkyl groups, respectively. The carbon atom by which indicated moiety is attached is a secondary, tertiary, and quaternary carbon atom, respectively.

A cycloalkane is a saturated cyclic hydrocarbon, with or without side chains (e.g., cyclobutane or methylcyclobutane). Unsaturated cyclic hydrocarbons having at least one non-aromatic endocyclic carbon-carbon double or one triple bond are cycloalkenes and cycloalkynes, respectively. Unsaturated cyclic hydrocarbons having more than one such multiple bond can further specify the number and/or position(s) of such multiple bonds (e.g., cycloalkadienes, cycloalkatrienes, and so forth). The unsaturated cyclic hydrocarbons may be further identified by the position of the carbon-carbon multiple bond(s)

A "cycloalkyl group" is a univalent group derived by removing a hydrogen atom from a ring carbon atom from a cycloalkane. For example, a 1-methylcyclopropyl group and a 2-methylcyclopropyl group are illustrated as follows.

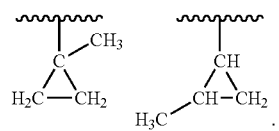

A "cycloalkylene group" refers to a group derived by removing two hydrogen atoms from a cycloalkane, at least one of which is a ring carbon. Thus, a "cycloalkylene group" includes a group derived from a cycloalkane in which two hydrogen atoms are formally removed from the same ring carbon, a group derived from a cycloalkane in which two hydrogen atoms are formally removed from two different ring carbons, and a group derived from a cycloalkane in which a first hydrogen atom is formally removed from a ring carbon and a second hydrogen atom is formally removed from a carbon atom that is not a ring carbon. A "cycloalkane group" refers to a generalized group formed by removing one or more hydrogen atoms (as necessary for the particular group and at least one of which is a ring carbon) from a cycloalkane.

The term "alkene" whenever used in this specification and claims refers to a compound that has at least one non-aromatic carbon-carbon double bond. The term "alkene" includes aliphatic or aromatic, cyclic or acyclic, and/or linear and branched alkenes unless expressly stated otherwise. The term "alkene," by itself, does not indicate the presence or absence of heteroatoms and/or the presence or absence of other carbon-carbon double bonds unless explicitly indicated. The terms "hydrocarbon alkene" or "alkene hydrocarbon" refer to alkenes containing only hydrogen and carbon. Other identifiers may be utilized to indicate the presence or absence of particular groups within an alkene. Alkenes may also be further identified by the position of the carbon-carbon double bond. Alkenes, having more than one such multiple bond are alkadienes, alkatrienes, and so forth. The alkene may be further identified by the position(s) of the carbon-carbon double bond(s).

An "alkenyl group" is a univalent group derived from an alkene by removal of a hydrogen atom from any carbon atom of the alkene. Thus, "alkenyl group" includes groups in which the hydrogen atom is formally removed from an $sp^2$ hybridized (olefinic) carbon atom and groups in which the hydrogen atom is formally removed from any other carbon atom. For example and unless otherwise specified, propen-1-yl (—CH=CHCH$_3$), propen-2-yl [(CH$_3$)C=CH$_2$], and propen-3-yl (—CH$_2$CH=CH$_2$) groups are all encompassed with the term "alkenyl group." Similarly, an "alkenylene group" refers to a group formed by formally removing two hydrogen atoms from an alkene, either two hydrogen atoms from one carbon atom or one hydrogen atom from two different carbon atoms. An "alkene group" refers to a generalized group formed by removing one or more hydrogen atoms (as needed for the particular group) from an alkene. When the hydrogen atom is removed from a carbon atom participating in a carbon-carbon double bond, the regiochemistry of the carbon from which the hydrogen atom is removed, and regiochemistry of the carbon-carbon double bond may both be specified. The terms "alkenyl group," "alkenylene group," and "alkene group" by themselves do not indicate the presence or absence of heteroatoms and/or the presence or absence of other carbon-carbon double bonds unless explicitly indicated. The terms "hydrocarbon alkenyl group," "hydrocarbon alkenylene group," and "hydrocarbon alkene group" refer to alkene groups containing only hydrogen and carbon. Other identifiers may be utilized to indicate the presence or absence of particular groups within an alkene group. Alkenyl groups may also have more than one such multiple bond. The alkene group may also be further identified by the position(s) of the carbon-carbon double bond(s).

The term "alkyne" is used in this specification and claims to refer to a compound that has at least one carbon-carbon triple bond. The term "alkyne" includes aliphatic or aromatic, cyclic or acyclic, and/or linear and branched alkynes unless expressly stated otherwise. The term "alkyne," by itself, does not indicate the presence or absence of heteroatoms and/or the presence or absence of other carbon-carbon triple bonds unless explicitly indicated. The terms "hydrocarbon alkyne" or "alkyne hydrocarbon" refer to alkyne compounds containing only hydrogen and carbon. Other identifiers may be utilized to indicate the presence or absence of particular groups within an alkyne. Alkynes, having more than one such multiple bond are alkadiynes, alkatriynes, and so forth. The alkyne group may also be further identified by the position(s) of the carbon-carbon triple bond(s).

An "alkynyl group" is a univalent group derived from an alkyne by removal of a hydrogen atom from any carbon atom of the alkyne. Thus, "alkynyl group" includes groups in which the hydrogen atom is formally removed from an sp hybridized (acetylenic) carbon atom and groups in which the hydrogen atom is formally removed from any other carbon atom. For example and unless otherwise specified, 1-propyn-1-yl (—C≡CCH$_3$) and propyn-3-yl (HC≡CCH$_2$—) groups are encompassed with the term "alkynyl group." Similarly, an "alkynylene group" refers to a group formed by formally removing two hydrogen atoms from an alkyne, either two hydrogen atoms from one carbon atom if possible or one hydrogen atom from two different carbon atoms. An "alkyne group" refers to a generalized group formed by removing one or more hydrogen atoms (as needed for the particular group) from an alkyne. The terms "alkynyl group," "alkynylene group," and "alkyne group" by themselves do not indicate the presence or absence of heteroatoms and/or the presence or absence of other carbon-carbon double bonds unless explicitly indicated. The terms "hydrocarbon alkynyl group," "hydrocarbon alkynylene group," and "hydrocarbon alkyne group" refer to olefin groups containing only hydrogen and carbon. Other identifiers may be utilized to indicate the presence or absence of particular groups within an alkyne group. Alkyne groups may have more than one such multiple bond. Alkyne groups may also be further identified by the position(s) of the carbon-carbon triple bond(s).

An "aromatic group" refers to a generalized group formed by removing one or more hydrogen atoms (as needed for the particular group and at least one of which is an aromatic ring carbon atom) from an aromatic compound. Thus, an "aromatic group" as used herein refers to a group derived by removing one or more hydrogen atoms from an aromatic compound, that is, a compound containing a cyclically conjugated hydrocarbon that follows the Hückel (4n+2) rule and containing (4n+2) pi-electrons, where n is an integer from 1 to about 5. Aromatic compounds and hence "aromatic groups" may be monocyclic or polycyclic unless otherwise specified. Aromatic compounds include "arenes" (hydrocarbon aromatic compounds) and "heteroarenes," also termed "hetarenes" (heteroaromatic compounds formally derived from arenes by replacement of one or more methine (—C=) carbon atoms by trivalent or divalent heteroatoms, in such a way as to maintain the continuous pi-electron system characteristic of aromatic systems and a number of out-of-plane pi-electrons corresponding to the Hückel rule (4n+2). While arenes and heteroarenes are mutually exclusive members of the group of aromatic compounds, a compound that has both an arene group and a heteroarene group that compound generally is considered a heteroarene compound. Aromatic compounds, arenes, and heteroarenes may be mono- or polycyclic unless otherwise specified. Examples of arenes include, but are not limited to, benzene, naphthalene, and toluene, among others. Examples of heteroarenes include, but are not limited to furan, pyridine, and methylpyridine, among others. As disclosed herein, the term "substituted" may be used to describe an aromatic group wherein any non-hydrogen moiety formally replaces a hydrogen in that group, and is intended to be non-limiting.

An "aryl group" refers to a generalized group formed by removing a hydrogen atom from an aromatic hydrocarbon ring carbon atom from an arene. One example of an "aryl group" is ortho-tolyl (o-tolyl), the structure of which is shown here.

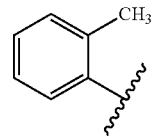 [SMILES: *c1ccccc1C]

Similarly, an "arylene group" refers to a group formed by removing two hydrogen atoms (at least one of which is from an aromatic hydrocarbon ring carbon) from an arene. An "arene group" refers to a generalized group formed by removing one or more hydrogen atoms (as needed for the particular group and at least one of which is an aromatic hydrocarbon ring carbon) from an arene. However, if a group contains separate and distinct arene and heteroarene rings or ring systems (e.g., the phenyl and benzofuran moieties in 7-phenylbenzofuran) its classification depends upon the particular ring or ring system from which the hydrogen atom was removed, that is, an arene group if the removed hydrogen came from the aromatic hydrocarbon ring or ring system carbon atom (e.g., the 2 carbon atom in the phenyl group of 6-phenylbenzofuran) and a heteroarene group if the removed hydrogen carbon came from a heteroaromatic ring or ring system carbon atom (e.g., the 2 or 7 carbon atom of the benzofuran group of 6-phenylbenzofuran).

An "aralkyl group" is an aryl-substituted alkyl group having a free valance at a non-aromatic carbon atom, for example, a benzyl group is an "aralkyl" group. Similarly, an "aralkylene group" is an aryl-substituted alkylene group having two free valances at a single non-aromatic carbon atom or a free valence at two non-aromatic carbon atoms while an "aralkane group" is a generalized is an aryl-substituted alkane group having one or more free valances at a non-aromatic carbon atom(s). A "heteroaralkyl group" is a heteroaryl-substituted alkyl group having a free valence at a non-heteroaromatic ring or ring system carbon atom. Similarly a "heteroaralkylene group" is a heteroaryl-substituted alkylene group having a two free valances at a single non-heteroaromatic ring or ring system carbon atom or a free valences at two non-heteroaromatic ring or ring system carbon atoms while a "heteroaralkane group" is a generalized aryl-substituted alkane group having one or more free valances at a non-heteroaromatic ring or ring system carbon atom(s).

If a compound or group contains more than one moiety it is formally a member of the group having the highest naming priority as stipulated by IUPAC. For example 4-phenylpyridine is a heteroaromatic compound and a 4-(phen-2-ylene)pyridin-2-yl group is a heteroaromatic group because the highest naming groups is the pyridine group and the pyridin-2-yl group respectively.

A silane is a compound containing a silicon atom. A "silyl group" is a generalized group formed by removing a hydrogen atom from the silicon atom of a silane.

The terms "contact product," "contacting," and the like, are used herein to describe compositions wherein the components are contacted together in any order, in any manner, and for any length of time. For example, the components can be contacted by blending or mixing. Further, unless otherwise specified, the contacting of any component can occur in the presence or absence of any other component of the compositions described herein. Combining additional materials or components can be done by any suitable method. Further, the term "contact product" includes mixtures, blends, solutions, slurries, reaction products, and the like, or combinations thereof. Although "contact product" can, and often does, include reaction products, it is not required for the respective components to react with one another. Likewise, "contacting" two or more components can result in a reaction product or a reaction mixture. Consequently, depending upon the circumstances, a "contact product" can be a mixture, a reaction mixture, or a reaction product.

Although any methods and materials similar or equivalent to those described herein can be used in the practice or testing of the invention, the typical methods and materials are herein described.

All publications and patents mentioned herein are incorporated herein by reference for the purpose of describing and disclosing, for example, the constructs and methodologies that are described in the publications, which might be used in connection with the presently described invention. The publications discussed throughout the text are provided solely for their disclosure prior to the filing date of the present application. Nothing herein is to be construed as an admission that the inventors are not entitled to antedate such disclosure by virtue of prior invention.

DETAILED DESCRIPTION OF THE INVENTION

The present invention provides methods of synthesizing substituted pyrroles from substituted furans.

Direct Conversion of a Substituted Furan Compound to a Substituted Pyrrole Compound Embodiments of this invention are directed to processes for producing a substituted pyrrole compound. In particular, processes for producing a pyrrole compound having a substituent at the 2, 3, 4, and/or 5 position of the pyrrole ring are disclosed. Such processes can comprise (or consist essentially of, or consist of):

1) contacting
  a) a substituted furan compound;
  b) ammonia, an ammonium salt, or a combination thereof; and
  c) a catalyst; and
2) forming the substituted pyrrole compound.

Generally, the features of the process (e.g., the substituted furan or substituted pyrrole compound, the ammonia or ammonium salt, the catalyst, the ratios of the respective components, and the conditions under which the substituted pyrrole compound is formed, among others) are independently described herein, and these features may be combined in any combination to further describe the process.

In some embodiments, the contacting step (step 1 of the process) can include contacting the substituted furan compound; the ammonia, ammonium salt, or combinations thereof; and the catalyst; and additional unrecited materials (e.g., water, an organic solvent, etc.). In other embodiments, the contacting step can consist essentially of contacting the substituted furan compound; the ammonia, ammonium salt, or combinations thereof; and the catalyst. Alternatively, the contacting step can consist of contacting the substituted furan compound; the ammonia, ammonium salt, or combinations thereof; and the catalyst. Likewise, additional materials or features can be employed in the forming step (step 2 of the process). For instance, the formation of the substituted pyrrole compound can occur in the presence of water, or in the presence of an organic solvent, or in the presence of a water scavenger, each of which will be discussed further herein. Further, it is contemplated that the processes for producing substituted pyrrole compounds can employ more than one substituted furan compound and/or more than one catalyst. Additionally, a combination of ammonia and an ammonium salt, or a combination of two or more ammonium salts, can be employed.

In the processes disclosed herein, the equivalent ratio of ammonia and/or the ammonium salt to the substituted furan compound can be in a range from 0.9:1 to 200:1, from 0.95:1 to 100:1, or from 0.975:1 to 50:1. In some embodiments, the equivalent ratio of ammonia and/or the ammonium salt to the substituted furan compound can be in a range from 0.99:1 to 25:1, while in other embodiments, the equivalent ratio of ammonia and/or the ammonium salt to the substituted furan compound can be in a range from 1:1 to 20:1. Equivalent ratios of ammonia and/or the ammonium salt to the substituted furan compound of greater than 0.9:1, greater than 0.95:1, greater than 0.975:1, greater than 0.99:1, greater than 1:1, or greater than 1.1:1, also can be employed in embodiments of this invention.

Independently, the contacting and forming steps of the process for producing a substituted pyrrole compound can be conducted at a variety of temperatures, pressures, and time periods. For instance, the temperature at which the substituted furan, the ammonia and/or ammonium salt, and the catalyst are initially contacted can be the same as, or different from, the temperature at which the substituted pyrrole compound is formed. As an illustrative example, in the contacting step, the substituted furan compound, the ammonia and/or ammonium salt, and the catalyst can be contacted initially at temperature T1 and, after this initial combining, the temperature can be increased to a temperature T2 to allow the formation of the substituted pyrrole compound. Likewise, the pressure can be different in the contacting step and the forming step. Often, the time period in the contacting step can be referred to as the contact time, while the time period in forming step can be referred to as the reaction time. The contact time and the reaction time can be, and often are, different.

In an embodiment, the contacting step of the process for producing a substituted pyrrole can be conducted at a temperature in a range from 0° C. to 500° C.; alternatively, from 25° C. to 500° C.; alternatively, from 40° C. to 450° C.; alternatively, from 50° C. to 400° C.; alternatively, from 75° C. to 400° C.; or alternatively, from 100° C. to 400° C. In these and other embodiments, after the initial contacting, the temperature can be changed, if desired, to another temperature for the formation of the substituted pyrrole compound.

Accordingly, the step of forming the substituted pyrrole can be conducted at a temperature in a range from 0° C. to 500° C.; alternatively, from 25° C. to 500° C.; alternatively, from 40° C. to 450° C.; alternatively, from 50° C. to 400° C.; alternatively, from 75° C. to 400° C.; or alternatively, from 100° C. to 400° C. These temperature ranges also are meant to encompass circumstances where the step of forming the substituted pyrrole compound can be conducted at a series of different temperatures, instead of at a single fixed temperature, falling within the respective ranges.

In an embodiment, the contacting step and/or the step of forming a substituted pyrrole compound can be conducted at a total reactor pressure in a range from 5 to 5000 psig, such as, for example, from 15 to 4000 psig. In some embodiments, the formation of the substituted pyrrole compound can be conducted at total reactor pressure in a range from 25 to 3500 psig; alternatively, from 50 to 3000 psig; alternatively, from 75 to 3000 psig; or alternatively, from 100 to 2000 psig.

The contacting step of the process is not limited to any particular duration of time. That is, the substituted furan, the ammonia and/or ammonium salt, and the catalyst can be initially contacted rapidly, or over a longer period of time, before commencing the reaction and/or the formation of the substituted pyrrole compound. Hence, the contacting step can be conducted, for example, in a time period ranging from as little as 1-30 seconds to as long as 1-12 hours. In non-continuous or batch operations, the appropriate reaction time for the step of forming the substituted pyrrole compound can depend upon, for example, the reaction temperature, the reaction pressure, and the ratios of the respective components in the contacting step, among other variables. Generally, however, the substituted pyrrole can be formed over a time period that can be in a range from 1 minute to 96 hours, such as, for example, from 2 minutes to 96 hours, from 5 minutes to 72 hours, from 10 minutes to 72 hours, or from 15 minutes to 48 hours.

If the process for producing a substituted pyrrole compound is a continuous process, then the furan-catalyst contact/reaction time can be expressed in terms of weight hourly space velocity (WHSV)—the ratio of the weight of the substituted furan compound which comes in contact with a given weight of catalyst per unit time. While not limited thereto, the WHSV employed for the process of producing a substituted pyrrole can be in a range from 0.05 to 100, or from 0.05 to 50, or from 0.075 to 50, or from 0.1 to 25.

The present invention contemplates any order of contacting the substituted furan, the ammonia and/or ammonium salt, and the catalyst. In an embodiment, the substituted furan, the ammonia and/or ammonium salt, and the catalyst are contacted substantially contemporaneously. In another embodiment, the substituted furan can be contacted with the catalyst for a period of time, prior to contacting the furan/catalyst mixture with the ammonia and/or ammonium salt. Yet, in another embodiment, the ammonia and/or ammonium salt can be contacted with the catalyst for a period of time, prior to contacting the catalyst/ammonia and/or ammonium salt mixture with the substituted furan. In still another embodiment, the ammonia and/or ammonium salt can be contacted with the substituted furan for a period of time, prior to contacting the substituted furan/ammonia and/or ammonium salt mixture with the catalyst. For instance, in a flow reactor or continuous process, the ammonia and/or ammonium salt can be contacted with the substituted furan for a period of time, and then pumped through a reactor containing the catalyst. In these embodiments, the contacting of any components can be conducted rapidly or over a longer period of time, for instance, from time periods ranging from as little as 1-30 seconds to as long as 1-48 hours. Hence, contacting times of about 1 sec, 30 sec, 1 min, 5 min, 10 min, 30 min, 1 hr, 2 hr, 6 hr, 12 hr, 24 hr, 36 hr, or 48 hr can be utilized in embodiments of the invention. Alternatively, the contacting time can range between any two of the contacting times provided herein.

The synthesis of a substituted pyrrole compound from the reaction of a substituted furan compound with ammonia and/or ammonium salt in the presence of a catalyst produces water. However, in embodiments of this invention, the substituted pyrrole can be produced in the presence of added water (in liquid or vapor form, depending upon the desired reaction conditions). In these embodiments, added water is any water which is not produced by the formation of the substituted pyrrole compound, and includes water which can be an impurity in any of the materials utilized in the process (e.g., substituted furan compound, ammonia, ammonium salt, catalyst, and/or solvent, among others), a component of any material utilized in the process (e.g., an aqueous ammonium salt), or a separately added reagent. In an embodiment, the maximum molar ratio of added water to the substituted furan compound can be 1,000:1. In other embodiments, the maximum molar ratio of added water to the substituted furan compound can be 750:1, 500:1, 250:1, 150:1, 100:1, 75:1, 50:1, 25:1, 15:1, or 10:1. In an embodiment, the maximum molar ratio of added water to the substituted furan compound can be 0.1:1, 0.25:1, 0.5:1, 0.75:1, 1:1, 2.5:1, or 5:1. Generally, the range of the added water can be from any minimum molar ratio of added water disclosed herein to any maximum molar ratio of added water disclosed herein. In some non-limiting embodiments, the synthesis of the substituted pyrrole compound can be performed in a molar ratio of added water ranging from 0.01:1 to 1,000:1; alternatively, ranging from 0.25:1 to 750:1; or alternatively, ranging from 0.5:1 to 500:1. Other ranges of added water are apparent based upon the maximum molar ratios of added water and minimum molar ratios of added water presented in this disclosure. In some embodiments, the added water can be introduced in the contacting step of the process to produce a substituted pyrrole compound. In other embodiments, the added water can be introduced in combination with another reagent of the process (e.g., as a component of a composition comprising an ammonium salt).

Additionally, or alternatively, the pyrrole compound can be formed in the presence of an organic solvent. Typically, when used, the organic solvent can be present in an amount up to 1,000 wt. %, based on the weight of the substituted furan compound. Alternatively, the substituted pyrrole compound can be produced in the presence of an organic solvent in an amount up to 750 wt. %, up to 500 wt. %, up to 250 wt. %, up to 200 wt. %, up to 150 wt. %, or up to 100 wt. %. When an organic solvent is utilized, the minimum amount of organic solvent can be at least 5 wt. %, at least 10 wt. %, at least 25 wt. %, at least 50 wt. %, or at least 75 wt. %, based on the weight of the substituted furan compound. Generally, the range of organic solvent which can be utilized can range from any minimum amount of organic solvent disclosed herein to any maximum amount of organic solvent disclosed herein. In some non-limiting embodiments, the synthesis of the substituted pyrrole compound can be performed in the presence of an organic solvent in an amount of from 5 wt. % to 1,000 wt. %, from 10 wt. % to 750 wt. %, from 25 wt. % to 500 wt. %, from 50 wt. % to 250 wt. %, from 50 wt. % to 150 wt. %, or from 75 wt. % to 125 wt. %, based on the weight of the substituted furan compound. Other ranges of organic solvent are apparent based upon the maximum molar ratios of added water and minimum molar ratios of added water presented in this disclosure. The organic solvent can be contacted with the substituted furan, the ammonia and/or ammonium salt, and the catalyst in the contacting step of the process, and remain present during the formation of the substituted pyrrole compound. Alternatively, the organic solvent can be added after the initial contacting in step 1. Organic solvents which can be utilized as the solvent are described herein, and these organic solvents can be utilized without limitation in the processes described herein.

In another embodiment, the substituted pyrrole compound can be formed in the substantial absence of added water. In this instance, the added water can enter the process as an impurity in any of the materials utilized in the process (e.g., substituted furan compound, ammonia, ammonium salt, catalyst, and/or solvent, among others). As used herein, a "substantial absence of added water" means a molar ratio of the added water to the substituted furan compound of less than 0.1:1. Therefore, the substituted pyrrole can be formed at molar ratio of added water to substituted furan compound of less than 0.075:1, less than 0.05:1, less than 0.025:1, or less than 0.01:1.

In yet another embodiment, the substituted pyrrole compound can be formed in the substantial absence of an organic solvent. As used herein, a "substantial absence of organic solvent" means less than 5% by weight, based on the weight of the substituted furan compound. Therefore, the substituted pyrrole can be synthesized in the presence of less than 5% by weight, less than 4% by weight, less than 3% by weight, less than 2% by weight, or less than 1% by weight, of organic solvent based on the weight of the substituted furan compound. It is also contemplated that the process can be conducted with no added water and/or no added organic solvent.

In a further embodiment, it is contemplated that the process can be conducted in the presence of a water scavenger, the purpose of which can be to remove water formed during the reaction of the substituted furan with the ammonia and/or ammonium salt in the presence of a catalyst. Examples of suitable water scavengers include, but are not limited to, a water reactive reagent, a water absorbent, or any combination thereof; alternatively, a water reactive reagent; or alternatively, a water absorbent.

In an embodiment, the water reactive reagent can be a titanium halide, a zirconium halide, a boron halide, an aluminum halide, a silicon halide, a phosphorus halide, a phosphoryl halide, phosphorus pentaoxide, an oxalyl halide, halosulfonic acid, a thionyl halide, an acid halide of a carboxylic acid, an anhydride of a carboxylic acid, or any combination thereof. In other embodiments, the water reactive reagent can be a titanium halide, a zirconium halide, an aluminum halide, a silicon halide, a phosphorus halide, or any combination thereof; alternatively, a phosphoryl halide, a oxalyl halide, halosulfonic acid, a thionyl halide, an acid halide of a carboxylic acid, an anhydride of a carboxylic acid, or any combination thereof; alternatively, a titanium halide; alternatively, a zirconium halide; alternatively, a boron halide; alternatively, an aluminum halide; alternatively, a silicon halide; alternatively, a phosphorus halide, phosphorus pentaoxide, or a phosphoryl halide; alternatively, a phosphorus halide; alternatively, phosphorus pentaoxide; alternatively, a phosphoryl halide; alternatively, a oxalyl halide; alternatively, halosulfonic acid; alternatively, a thionyl halide; alternatively, an acid halide of a carboxylic acid or an anhydride of a carboxylic acid; alternatively, an acid halide of a carboxylic acid; or alternatively, an anhydride of a carboxylic acid. In an embodiment, the halide of any of the water reactive agents can be fluoride, chloride, bromide, or iodide; alternatively, chloride or bromide; alternatively, fluoride, alternatively, chloride; alternatively, bromide; or alternatively, iodide. In an embodiment, the water reactive reagent can be titanium tetrachloride, zirconium tetrachloride, boron trifluoride, boron trichloride, aluminum trichloride, aluminum tribromide, chlorotrimethylsilane, dichlorodimethylsilane, trichloromethylsilane, tetrachlorosilane, phosphorus pentachloride, phosphorus pentabromide, phosphorus trichloride, phosphorus tribromide, phosphorus pentaoxide, phosphoryl chloride, oxalyl chloride, chlorosulfonic acid, thionyl chloride, thionyl bromide, acetic anhydride, acetyl chloride, or any combination thereof. In other embodiments, the water reactive reagent can be titanium tetrachloride, zirconium tetrachloride, or a combination thereof; alternatively, boron trifluoride, boron trichloride, or a combination thereof; alternatively, aluminum trichloride, aluminum tribromide, or a combination thereof; alternatively, chlorotrimethylsilane, dichlorodimethylsilane, trichloromethylsilane, tetrachlorosilane, or any combination thereof; alternatively, phosphorus pentachloride, phosphorus pentabromide, phosphorus trichloride, phosphorus tribromide, or any combination thereof; alternatively, acetic anhydride, acetyl chloride, or a combination thereof; alternatively, titanium tetrachloride; alternatively, zirconium tetrachloride; alternatively, boron trifluoride; alternatively, boron trichloride; alternatively, aluminum trichloride; alternatively, aluminum tribromide; alternatively, chlorotrimethylsilane; alternatively, dichlorodimethylsilane; alternatively, trichloromethylsilane; alternatively, tetrachlorosilane; alternatively, phosphorus pentachloride; alternatively, phosphorus pentabromide; alternatively, phosphorus trichloride; alternatively, phosphorus tribromide; alternatively, phosphorus pentaoxide; alternatively, phosphoryl chloride; alternatively, oxalyl chloride; alternatively, chlorosulfonic acid; alternatively, thionyl chloride; alternatively, thionyl bromide; alternatively, acetic anhydride; or alternatively, acetyl chloride.

In an embodiment, the water absorbent can be a water absorbent metal salt, a superabsorbent polymer, a molecular sieve, silica, silica gel, a desiccant clay, or any combination thereof; alternatively, a water absorbent metal salt; alternatively, a superabsorbent polymer; alternatively, a molecular sieve; alternatively, silica or silica gel; alternatively, silica; alternatively, silica gel; or alternatively, a desiccant clay. In an embodiment, the water absorbent metal salt can be sodium sulfate, calcium sulfate, magnesium sulfate, or any combination thereof; alternatively, sodium sulfate; alternatively, calcium sulfate; or alternatively, magnesium sulfate. Exemplary molecular sieves include, but are not limited to, 3 Å molecular sieves, 4 Å molecular sieves, 13× molecular sieves, or any combination thereof; alternatively, 3 Å molecular sieves; alternatively, 4 Å molecular sieves; or alternatively, 13× molecular sieves.

In the processes for producing a substituted pyrrole compound described herein, it is contemplated that at least 5 wt. %, at least 8 wt. %, or at least 10 wt. %, of the substituted furan compound can be converted to the substituted pyrrole compound. Often, the conversion of substituted furan to substituted pyrrole is in a range from 5 wt. % to 95 wt. %; alternatively, from 8 wt. % to 90 wt. %; alternatively, from 10 wt. % to 90 wt. %; or alternatively, from 15 wt. % to 85 wt. %.

Typically, the substituted pyrrole can be produced at a weight ratio of the substituted pyrrole to furan-derived reaction by-products in a range from 0.25:1 to 20:1. In some embodiments, the weight ratio of the substituted pyrrole to furan-derived reaction byproducts can be in a range from 0.5:1 to 10:1; alternatively, from 1:1 to 10:1; alternatively, from 3:1 to 10:1; or alternatively, from 3:1 to 5:1. Furan-derived reaction by-products, in this context, is meant to include by-products derived from the substituted furan (or the pyrroles produced from the substituted furan—excluding the expected substituted pyrrole(s)), which have both longer and shorter retention times, as measured via gas chromatography. Water, materials resulting from the organic solvent, materials resulting from the reaction of water with a water scavenger, as well as residual reactants (e.g., ammonia) are not included as furan-derived reaction by-products.

The process for synthesizing a substituted pyrrole compound can be conducted in a variety of reactor configurations, such as stirred tanks and/or tubular vessels, including combinations of more than one reactor, in parallel or series, but is not limited thereto. Both batch and continuous processes/reactors are contemplated. In some embodiments, both step 1 and step 2 of the process are conducted in a single reactor, e.g., a one-pot synthesis of the substituted pyrrole.

Once formed, the substituted pyrrole compound can be purified and/or isolated and/or separated using suitable techniques which include, but are not limited to, evaporation, distillation, crystallization, extraction, washing, decanting, filtering, drying, and the like, including combinations of more than one of these techniques. In one embodiment, the process for producing a substituted pyrrole compound can further comprise a step of separating or isolating the substituted pyrrole compound from the reaction mixture formed from contacting and reacting the substituted furan, the ammonia and/or ammonium salt, and the catalyst.

Substituted Furan and Substituted Pyrrole Compounds

Embodiments of this invention are directed to processes for producing a substituted pyrrole compound, and these processes can comprise (or consist essentially of, or consist of) contacting a substituted furan compound; ammonia, an ammonium salt, or a combination thereof; and a catalyst; and producing the substituted pyrrole compound. In an embodiment, the substituted furan compound (also called the "substituted furan") can comprise, consist essentially of, or consist of, any substituted furan compound that can react to produce a substituted pyrrole compound. As used in this disclosure, the term "substituted furan compound" includes substituted furans, such as 2,5-dimethylfuran, but does not include furan ($C_4H_4O$). Similarly, as used in this disclosure, the term "substituted pyrrole compound" (also called the "substituted pyrrole") includes substituted pyrroles, such as 2,5-dimethylpyrrole, but does not include pyrrole ($C_4H_5N$).

Generally, the substituted furan compound and the substituted pyrrole compound can be a $C_4$ to $C_{20}$, or $C_4$ to $C_{10}$ substituted furan or substituted pyrrole. For example, substituted pyrrole compounds that can be produced by the processes disclosed herein can include, but are not limited to, 2,5-dimethylpyrrole, 2-methyl-5-ethylpyrrole, 2,5-diethylpyrrole, 2-ethyl-5-methylpyrrole, 2-ethyl-5-n-propylpyrrole, 2,5-di-n-propylpyrrole, 2,5-diisopropylpyrrole, 2,5-di-n-butylpyrrole, 2,5-di-n-pentylpyrrole, 2,5-di-n-hexylpyrrole, 2,5-di-n-heptylpyrrole, 2,5-di-n-octylpyrrole, 2,3,5-triethylpyrrole, 2,3,5-tri-n-butylpyrrole, 2,3,5-tri-n-pentylpyrrole, 2,3,5-tri-n-hexylpyrrole, 2,3,5-tri-n-heptylpyrrole, 2,3,5-tri-n-octylpyrrole, 2,3,4,5-tetraethylpyrrole, 2,3,4,5-tetra-n-butylpyrrole, 2,3,4,5-tetra-n-hexylpyrrole, 2,5-dibenzylpyrrole, 2,4-dimethylpyrrole, 2-methyl-4-isopropylpyrrole, 2,4-dimethyl-3-ethylpyrrole, 2,4-diethylpyrrole, 2-ethyl-4-isopropylpyrrole, 2-methyl-4-sec-butylpyrrole, 2-ethyl-4-sec-butylpyrrole, 2-methyl-4-isobutylpyrrole, 2-ethyl-4-isobutylpyrrole, 2-methyl-4-t-butylpyrrole, 2-ethyl-4-t-butylpyrrole, 2-methyl-4-neopentylpyrrole, 2-ethyl-4-neopentylpyrrole, 3,4-dimethylpyrrole, 3,4-diethylpyrrole, 3,4-diisopropylpyrrole, 3,4-di-sec-butylpyrrole, 3,4-diisobutylpyrrole, 3,4-di-t-butylpyrrole, 3,4-di-neopentylpyrrole, and the like, or any combination thereof. In addition, substituted pyrrole compounds such as pyrrole-2-carboxylic acid, 2-acetylpyrrole, pyrrole-2-carboxaldehyde, 3-acetyl-2,4-dimethylpyrrole, ethyl-2,4-dimethyl-5-(ethoxycarbonyl)-3-pyrrole-proprionate, ethyl-3,5-dimethyl-2-pyrrolecarboxylate, 3,4-dichloropyrrole, 2,3,4,5-tetrachloropyrrole, and combinations thereof, among others, can be produced utilizing the processes disclosed herein.

In an embodiment, the substituted furan compound and the substituted pyrrole compound can formula F1 and P1, respectively:

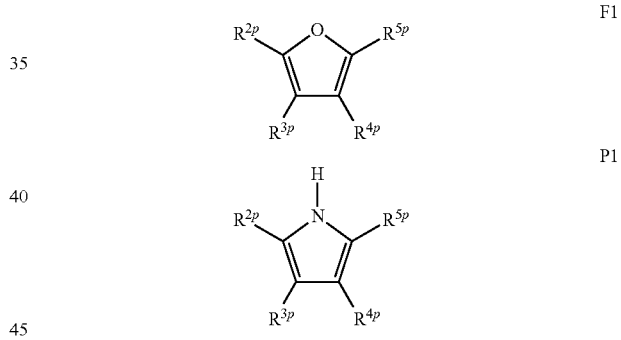

In formulas F1 and P1, $R^{2p}$, $R^{3p}$, $R^{4p}$, and $R^{5p}$ independently can be a hydrogen atom, a $C_1$-$C_{30}$ organyl group, or a $C_3$-$C_{60}$ silyl group. However, in all cases, at least one of $R^{2p}$, $R^{3p}$, $R^{4p}$, and $R^{5p}$ is not a hydrogen atom. In some embodiments, $R^{2p}$, $R^{3p}$, $R^{4p}$, and $R^{5p}$ independently can be a hydrogen atom, a $C_1$ to $C_{18}$ organyl group, or a $C_3$ to $C_{45}$ silyl group; alternatively, a hydrogen atom, a $C_1$ to $C_{10}$ organyl group, or a $C_3$ to $C_{30}$ silyl group; alternatively, a hydrogen atom, a $C_1$ to $C_5$ organyl group, or a $C_3$ to $C_{15}$ silyl group; alternatively, a hydrogen atom or a $C_1$ to $C_{18}$ organyl group; alternatively, a hydrogen atom or a $C_1$ to $C_{15}$ organyl group; alternatively, a hydrogen atom or a $C_1$ to $C_{10}$ organyl group; or alternatively, a hydrogen atom or a $C_1$ to $C_5$ organyl group. In an embodiment, $R^{2p}$, $R^{3p}$, $R^{4p}$, and $R^{5p}$ independently can be a hydrogen atom, a $C_1$ to $C_{30}$ hydrocarbyl group, or a $C_3$ to $C_{60}$ silyl group; alternatively, a hydrogen atom, a $C_1$ to $C_{18}$ hydrocarbyl group, or a $C_3$ to $C_{45}$ silyl group; alternatively, a hydrogen atom, a $C_1$ to $C_{10}$ hydrocarbyl group, or a $C_3$ to $C_{35}$ silyl group; alternatively, a hydrogen atom, a $C_1$ to $C_5$ hydrocarbyl group, or a $C_3$ to $C_{15}$ silyl group; alternatively, a hydrogen atom or a $C_1$ to $C_{18}$ hydrocarbyl group; alternatively, a hydrogen atom or a $C_1$ to $C_{15}$ hydrocarbyl group; alternatively, a hydrogen atom or a $C_1$ to $C_{10}$ hydrocarbyl group; or alternatively, a hydrogen atom or a $C_1$ to $C_5$ hydrocarbyl group.

In another embodiment, $R^{3p}$ and $R^{4p}$ can be hydrogen and $R^{2p}$ and $R^{5p}$ can be any non-hydrogen furan or pyrrole substituent described herein; alternatively, $R^{2p}$ and $R^{5p}$ can be hydrogen and $R^{3p}$ and $R^{4p}$ can be any non-hydrogen furan or pyrrole substituent described herein; or alternatively, $R^{2p}$ and $R^{4p}$ can be hydrogen and $R^{3p}$ and $R^{5p}$ can be any non-hydrogen furan or pyrrole substituent described herein. In some embodiments, $R^{2p}$, $R^{3p}$, and $R^{5p}$ can be hydrogen and $R^{4p}$ can be any non-hydrogen furan or pyrrole substituent described herein; alternatively, $R^{2p}$, $R^{3p}$, and $R^{4p}$ can be hydrogen and $R^{5p}$ can be any non-hydrogen furan or pyrrole substituent described herein; alternatively, $R^{2p}$ can be hydrogen and $R^{3p}$, $R^{4p}$, and $R^{5p}$ can be any non-hydrogen furan or pyrrole substituent described herein; or alternatively, $R^{3p}$ can be hydrogen and $R^{2p}$, $R^{4p}$, and $R^{5p}$ can be any non-hydrogen furan or pyrrole substituent described herein. In other embodiments, $R^{2p}$, $R^{3p}$, $R^{4p}$, and $R^{5p}$ can be any non-hydrogen furan or pyrrole substituent described herein.

In another embodiment, each non-hydrogen group which can be utilized as $R^{2p}$, $R^{3p}$, $R^{4p}$, and/or $R^{5p}$ of formula F1 and formula P1 independently can be an alkyl group, a substituted alkyl group, a cycloalkyl group, a substituted cycloalkyl group, an aromatic group, a substituted aromatic group, an aryl group, a substituted aryl group, an aralkyl group, a substituted aralkyl group, or a silyl group; or alternatively, an alkyl group, a substituted alkyl group, a cycloalkyl group, a substituted cycloalkyl group, an aromatic group, a substituted aromatic group, an aryl group, a substituted aryl group, an aralkyl group, or a substituted aralkyl group. In other embodiments, each non-hydrogen group which can be utilized as $R^{2p}$, $R^{3p}$, $R^{4p}$, and/or $R^{5p}$ of formula F1 and formula P1 independently can be an alkyl group; alternatively, a substituted alkyl group; alternatively, a cycloalkyl group; alternatively, a substituted cycloalkyl group; alternatively, an aromatic group; alternatively, a substituted aromatic group; alternatively, an aryl group; alternatively, a substituted aryl group; alternatively, an aralkyl group; alternatively, a substituted aralkyl group; or alternatively, a silyl group. Generally, the alkyl group, substituted alkyl group, cycloalkyl group, substituted cycloalkyl group, aromatic group, substituted aromatic group, aryl group, substituted aryl group, aralkyl group, substituted aralkyl group, and/or silyl group which can be utilized as a non-hydrogen $R^{2p}$, $R^{3p}$, $R^{4p}$, and/or $R^{5p}$ group of formula F1 and formula P1 can have the same number of carbons as its respective organyl group, hydrocarbyl group, or silyl group which can be utilized as a non-hydrogen $R^{2p}$, $R^{3p}$, $R^{4p}$, and/or $R^{5p}$ group of formula F1 and formula P1 disclosed herein.

Accordingly, in some embodiments, each alkyl group which can be utilized as a non-hydrogen $R^{2p}$, $R^{3p}$, $R^{4p}$, and/or $R^{5p}$ group of formula F1 and formula P1 can be a methyl group, an ethyl group, a propyl group, a butyl group, a pentyl group, a hexyl group, a heptyl group, an octyl group, a nonyl group, a decyl group, a undecyl group, a dodecyl group, a tridecyl group, a tetradecyl group, a pentadecyl group, a hexadecyl group, a heptadecyl group, an octadecyl group, or a nonadecyl group; or alternatively, a methyl group, an ethyl group, a propyl group, a butyl group, a pentyl group, a hexyl group, a heptyl group, an octyl group, a nonyl group, or a decyl group. In some embodiments, each alkyl group which can be utilized as a non-hydrogen $R^{2p}$, $R^{3p}$, $R^{4p}$, and/or $R^{5p}$ group of formula F1 and formula P1 can be a methyl group, an ethyl group, a n-propyl group, an iso-propyl group, a n-butyl group, an iso-butyl group, a sec-butyl group, a tert-butyl group, a n-pentyl group, an isopentyl group, a sec-pentyl group, or a neopentyl group; alternatively, a methyl group, an ethyl group, an iso-propyl group, a tert-butyl group, or a neopentyl group; alternatively, a methyl group; alternatively, an ethyl group; alternatively, a n-propyl group; alternatively, an isopropyl group; alternatively, a tert-butyl group; or alternatively, a neopentyl group. In an embodiment, any of these alkyl groups can be substituted with a halide or hydrocarboxy group to form the substituted alkyl group which can be utilized as a non-hydrogen $R^{2p}$, $R^{3p}$, $R^{4p}$, and/or $R^{5p}$ group of formula F1 and formula P1. Substituent halides and hydrocarboxy groups are disclosed herein and can be utilized without limitation to further describe the substituted alkyl group which can be utilized as a non-hydrogen $R^{2p}$, $R^{3p}$, $R^{4p}$, and/or $R^{5p}$ group of formula F1 and formula P1.

In some embodiments, the cycloalkyl group or substituted cycloalkyl group which can be utilized as a non-hydrogen $R^{2p}$, $R^{3p}$, $R^{4p}$, and/or $R^{5p}$ group formula F1 and formula P1 can be a cyclobutyl group, a substituted cyclobutyl group, a cyclopentyl group, a substituted cyclopentyl group, a cyclohexyl group, a substituted cyclohexyl group, a cycloheptyl group, a substituted cycloheptyl group, a cyclooctyl group, or a substituted cyclooctyl group. In some embodiments, the cycloalkyl group or substituted cycloalkyl group which can be utilized as a non-hydrogen $R^{2p}$, $R^{3p}$, $R^{4p}$, and/or $R^{5p}$ group of formula F1 and formula P1 can be a cyclopentyl group, a substituted cyclopentyl group, a cyclohexyl group, or a substituted cyclohexyl group. In other embodiments, the cycloalkyl group or substituted cycloalkyl group which can be utilized a non-hydrogen $R^{2p}$, $R^{3p}$, $R^{4p}$, and/or $R^{5p}$ group of formula F1 and formula P1 can be a cyclobutyl group or a substituted cyclobutyl group; alternatively, a cyclopentyl group or a substituted cyclopentyl group; alternatively, a cyclohexyl group or a substituted cyclohexyl group; alternatively, a cycloheptyl group or a substituted cycloheptyl group; or alternatively, a cyclooctyl group or a substituted cyclooctyl group. In further embodiments, the cycloalkyl group or substituted cycloalkyl group which can be utilized as a non-hydrogen $R^{2p}$, $R^{3p}$, $R^{4p}$, and/or $R^{5p}$ group of formula F1 and formula P1 can be a cyclopentyl group; alternatively, a substituted cyclopentyl group; alternatively, a cyclohexyl group; or alternatively, a substituted cyclohexyl group. Substituents which can be utilized for the substituted cycloalkyl groups are independently disclosed herein and can be utilized without limitation to further describe the substituted cycloalkyl group which can be utilized as a non-hydrogen $R^{2p}$, $R^{3p}$, $R^{4p}$, and/or $R^{5p}$ group of formula F1 and formula P1.

In some embodiments, the aryl group(s) which can be utilized as a non-hydrogen $R^{2p}$, $R^{3p}$, $R^{4p}$, and/or $R^{5p}$ group of formula F1 and formula P1 can be a phenyl group, a substituted phenyl group, a naphthyl group, or a substituted naphthyl group. In an embodiment, the aryl group(s) which can be utilized as a non-hydrogen $R^{2p}$, $R^{3p}$, $R^{4p}$, and/or $R^{5p}$ group of formula F1 and formula P1 can be a phenyl group or a substituted phenyl group; alternatively, a naphthyl group or a substituted naphthyl group; alternatively, a phenyl group or a naphthyl group; or alternatively, a substituted phenyl group or a substituted naphthyl group. Substituents which can be utilized for the substituted phenyl groups or substituted naphthyl groups are independently disclosed herein and can be utilized without limitation to further describe the substituted phenyl groups or substituted naphthyl groups which can be utilized as a non-hydrogen $R^{2p}$, $R^{3p}$, $R^{4p}$, and/or $R^{5p}$ group of formula F1 and formula P1.

In an embodiment, the substituted phenyl group which can be utilized as a non-hydrogen $R^{2p}$, $R^{3p}$, $R^{4p}$, and/or $R^{5p}$ group of formula F1 and formula P1 can be a 2-substituted phenyl group, a 3-substituted phenyl group, a 4-substituted phenyl group, a 2,4-disubstituted phenyl group, a 2,6-disubstituted phenyl group, 3,5-disubstituted phenyl group, or a 2,4,6-trisubstituted phenyl group. In other embodiments, the substituted phenyl group which can be utilized a non-hydrogen $R^{2p}$, $R^{3p}$, $R^{4p}$, and/or $R^{5p}$ group of formula F1 and formula P1 can be a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group or a 2,6-disubstituted phenyl group; alternatively, a 2-substituted phenyl group; alternatively, a 3-substituted phenyl group; alternatively, a 4-substituted phenyl group; alternatively, a 2,4-disubstituted phenyl group; alternatively, a 2,6-disubstituted phenyl group; alternatively, 3,5-disubstituted phenyl group; or alternatively, a 2,4,6-trisubstituted phenyl group. Substituents which can be utilized for these specific substituted phenyl groups are independently disclosed herein and can be utilized without limitation to further describe these substituted phenyl groups which can be utilized as a non-hydrogen $R^{2p}$, $R^{3p}$, $R^{4p}$, and/or $R^{5p}$ group of formula F1 and formula P1.

In some embodiments, the aralkyl group(s) which can be utilized as a non-hydrogen $R^{2p}$, $R^{3p}$, $R^{4p}$, and/or $R^{5p}$ group of formula F1 and formula P1 can be a benzyl group or a substituted benzyl group. In an embodiment, the aralkyl group(s) which can be utilized as a non-hydrogen $R^{2p}$, $R^{3p}$, $R^{4p}$, and/or $R^{5p}$ group of formula F1 and formula P1 can be a benzyl group, or alternatively, a substituted benzyl group. Substituents which can be utilized for the substituted aralkyl groups are independently disclosed herein and can be utilized without limitation to further describe the substituted aralkyl groups which can be utilized as a non-hydrogen $R^{2p}$, $R^{3p}$, $R^{4p}$, and/or $R^{5p}$ group of formula F1 and formula P1.

In some embodiments, the silyl group(s) which can be utilized as a non-hydrogen $R^{2p}$, $R^{3p}$, $R^{4p}$, and/or $R^{5p}$ group of formula F1 and formula P1 can have formula Si1:

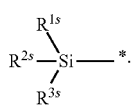

Si1

Generally, $R^{1s}$, $R^{2s}$, and $R^{3s}$ of the silyl group having formula Si1 independently can be an organyl group or a hydrocarbyl group; alternatively, an organyl group; or alternatively, a hydrocarbyl group. The organyl groups and/or the hydrocarbyl groups which can be utilized as $R^{1s}$, $R^{2s}$, and $R^{3s}$ of the silyl group having formula Si1 can have the numbers of carbons as those of the organyl groups and hydrocarbyl groups disclosed herein as non-hydrogen furan and pyrrole substituents. For instance, $R^{1s}$, $R^{2s}$, and $R^{3s}$ independently can be a $C_1$ to $C_{15}$ hydrocarbyl group. In an embodiment, $R^1$, $R^{2s}$, and $R^{3s}$ of the silyl group having formula Si1 independently can be an alkyl group, a substituted alkyl group, a cycloalkyl group, a substituted cycloalkyl group, an aromatic group, a substituted aromatic group, an aryl group, a substituted aryl group, an aralkyl group, or a substituted aralkyl group; alternatively, an alkyl group; alternatively, a substituted alkyl group; alternatively, a cycloalkyl group; alternatively, a substituted cycloalkyl group; alternatively, an aromatic group; alternatively, a substituted aromatic group; alternatively, an aryl group; alternatively, a substituted aryl group; alternatively, an aralkyl group; or alternatively, a substituted aralkyl group. Alkyl groups, substituted alkyl groups, cycloalkyl groups, substituted cycloalkyl groups, aromatic groups, substituted aromatic groups, aryl groups, substituted aryl groups, aralkyl groups, and substituted aralkyl groups have been independently described herein as potential non-hydrogen furan and pyrrole substituents and can be utilized, without limitation, as $R^{s1}$, $R^{s2}$, and $R^{s3}$ of the silyl group having formula Si1.

In an embodiment, each non-hydrogen substituent(s) for the substituted cycloalkyl group, substituted aromatic group, substituted aryl group, or substituted aralkyl group which can be utilized as a non-hydrogen $R^{2p}$, $R^{3p}$, $R^{4p}$, and/or $R^{5p}$ group of formula F1 and formula P1 independently can be a halide, a $C_1$ to $C_{10}$ hydrocarbyl group, or a $C_1$ to $C_{10}$ hydrocarboxy group; alternatively, a halide or a $C_1$ to $C_{10}$ hydrocarbyl group; alternatively, a halide or a $C_1$ to $C_{10}$ hydrocarboxy group; alternatively, a $C_1$ to $C_{10}$ hydrocarbyl group or a $C_1$ to $C_{10}$ hydrocarboxy group; alternatively, a halide; alternatively, a $C_1$ to $C_{10}$ hydrocarbyl group; or alternatively, a $C_1$ to $C_{10}$ hydrocarboxy group. In some embodiments, each non-hydrogen substituent(s) for the substituted cycloalkyl group, substituted aromatic group, substituted aryl group, or substituted aralkyl group which can be utilized as a non-hydrogen $R^{2p}$, $R^{3p}$, $R^{4p}$, and/or $R^{5p}$ group of formula F1 and formula P1 independently can be a halide, a $C_1$ to $C_5$ hydrocarbyl group, or a $C_1$ to $C_5$ hydrocarboxy group; alternatively, a halide or a $C_1$ to $C_5$ hydrocarbyl group; alternatively, a halide or a $C_1$ to $C_5$ hydrocarboxy group; alternatively, a $C_1$ to $C_5$ hydrocarbyl group or a $C_1$ to $C_5$ hydrocarboxy group; alternatively, a halide; alternatively, a $C_1$ to $C_5$ hydrocarbyl group; or alternatively, a $C_1$ to $C_5$ hydrocarboxy group. Specific substituent halides, hydrocarbyl groups, and hydrocarboxy groups are independently disclosed herein and can be utilized without limitation to further describe the substituents of the substituted cycloalkyl groups, substituted aromatic groups, substituted aryl groups, or substituted aralkyl groups which can be utilized as a non-hydrogen $R^{2p}$, $R^{3p}$, $R^{4p}$, and/or $R^{5p}$ group of formula F1 and formula P1.

In an embodiment, any halide substituent of a substituted alkyl group (general or specific), substituted cycloalkyl group (general or specific), substituted aromatic group (general or specific), substituted aryl group (general or specific), or substituted aralkyl group (general or specific) can be a fluoride, a chloride, a bromide, or an iodide; alternatively, a fluoride or a chloride. In some embodiments, any halide substituent of a substituted alkyl group (general or specific), substituted cycloalkyl group (general or specific), substituted aromatic group (general or specific), substituted aryl group (general or specific), or substituted aralkyl group (general or specific) can be a fluoride; alternatively, a chloride; alternatively, a bromide; or alternatively, an iodide.

In an embodiment, any hydrocarbyl substituent of a substituted cycloalkyl group (general or specific), substituted aromatic group (general or specific), substituted aryl group (general or specific), or substituted aralkyl group (general or specific) can be an alkyl group, an aryl group, or an aralkyl group; alternatively, an alkyl group; alternatively, an aryl group; or alternatively, an aralkyl group. Generally, the alkyl, aryl, and aralkyl substituent groups can have the same number of carbon atoms as the hydrocarbyl substituent groups disclosed herein. In an embodiment, any alkyl substituent of a substituted cycloalkyl group (general or specific), substituted aromatic group (general or specific), substituted aryl group (general or specific), or substituted aralkyl group (general or specific) can be a methyl group, an ethyl group, a n-propyl group, an isopropyl group, a n-butyl group, a sec-butyl group, an isobutyl group, a tert-butyl group, a n-pentyl group, a 2-pentyl group, a 3-pentyl group, a 2-methyl-1-butyl group, a tert-pentyl group, a 3-methyl-1-butyl group, a 3-methyl-2-butyl group, or a neo-pentyl group; alternatively, a methyl group, an ethyl group, an isopropyl group, a tert-butyl group, or a neo-pentyl group; alternatively, a methyl group; alternatively, an ethyl group; alternatively, an isopropyl group; alternatively, a tert-butyl group; or alternatively, a neo-pentyl group. In an embodiment, any aryl substituent of a substituted cycloalkyl group (general or specific), substituted aromatic group (general or specific), substituted aryl group (general or specific), or substituted aralkyl group (general or specific) can be a phenyl group, a tolyl group, a xylyl group, or a 2,4,6-trimethylphenyl group; alternatively, a phenyl group; alternatively, a tolyl group, alternatively, a xylyl group; or alternatively, a 2,4,6-trimethylphenyl group. In an embodiment, any aralkyl substituent of a substituted cycloalkyl group substituted cycloalkyl group (general or specific), substituted aromatic group (general of specific), substituted aryl group (general or specific), or substituted aralkyl group (general or specific) can be a benzyl group.

In an embodiment, any hydrocarboxy substituent of a substituted alkyl group (general or specific), substituted cycloalkyl group (general or specific), substituted aromatic group (general of specific), substituted aryl group (general or specific), or substituted aralkyl group (general or specific) can be an alkoxy group, an aryloxy group, or an aralkoxy group; alternatively, an alkoxy group; alternatively, an aryloxy group; or alternatively, an aralkoxy group. Generally, the alkoxy, aryloxy, and aralkoxy substituent groups can have the same number of carbon atoms as the hydrocarboxy substituent group disclosed herein. In an embodiment, any alkoxy substituent of a substituted alkyl group (general or specific), substituted cycloalkyl group (general or specific), substituted aromatic group (general of specific), substituted aryl group (general or specific), or substituted aralkyl group (general or specific) can be a methoxy group, an ethoxy group, a n-propoxy group, an isopropoxy group, a n-butoxy group, a sec-butoxy group, an isobutoxy group, a tert-butoxy group, a n-pentoxy group, a 2-pentoxy group, a 3-pentoxy group, a 2-methyl-1-butoxy group, a tert-pentoxy group, a 3-methyl-1-butoxy group, a 3-methyl-2-butoxy group, or a neo-pentoxy group; alternatively, a methoxy group, an ethoxy group, an isopropoxy group, a tert-butoxy group, or a neo-pentoxy group; alternatively, a methoxy group; alternatively, an ethoxy group; alternatively, an isopropoxy group; alternatively, a tert-butoxy group; or alternatively, a neopentoxy group. In an embodiment, any aryloxy substituent of a substituted alkyl group (general or specific), substituted cycloalkyl group (general or specific), substituted aromatic group (general of specific), substituted aryl group (general or specific), or substituted aralkyl group (general or specific) can be phenoxy group, a toloxy group, a xyloxy group, or a 2,4,6-trimethylphenoxy group; alternatively, a phenoxy group; alternatively, a toloxy group, alternatively, a xyloxy group; or alternatively, a 2,4,6-trimethylphenoxy group. In an embodiment, any aralkoxy substituent of a substituted alkyl group (general or specific), substituted cycloalkyl group (general or specific), substituted aromatic group (general of specific), substituted aryl group (general or specific), or substituted aralkyl group (general or specific) can be a benzoxy group.

In an embodiment, each silyl group(s) which can be utilized as a non-hydrogen $R^{2p}$, $R^{3p}$, $R^{4p}$, and/or $R^{5p}$ group of formula F1 and formula P1 can be a trihydrocarbylsilyl group. In some embodiments, each silyl group(s) which can be utilized as a non-hydrogen $R^{2p}$, $R^{3p}$, $R^{4p}$, and/or $R^{5p}$ group of formula F1 and formula P1 can be a trialkylsilyl group, a triphenylsilyl group, or a tri(substituted phenyl)silyl group; alternatively, a trialkylsilyl group; alternatively, a triphenylsilyl group; or alternatively, a tri(substituted phenyl)silyl group. Hydrocarbyl groups, alkyl groups, and substituted phenyl groups have been independently described herein as potential non-hydrogen furan and pyrrole substituents and can be utilized, without limitation, as $R^{s1}$, $R^{s2}$, and $R^{s3}$ of the silyl group having formula Si1.

In an embodiment, the substituted furan or substituted pyrrole compound can comprise, consist essentially of, or consist of, a substituted furan or substituted pyrrole compound having any non-hydrogen substituent group disclosed herein attached to the 2- and 5-positions of the furan or pyrrole. Unless otherwise specified, the substituted furan or substituted pyrrole compound having any non-hydrogen substituent group disclosed herein attached to the 2- and 5-positions, can have groups attached at the 3 and/or 4 positions. In an embodiment, the substituted furan or substituted pyrrole can be a 2,5-disubstituted furan or pyrrole compound, that is, the furan or pyrrole compound has substituents only at the 2- and 5-positions. Regardless of whether or not the substituted furan or substituted pyrrole compound has substituents present at the 3 and/or 4 positions, the groups attached to the 2- and 5-positions of the substituted furan or substituted pyrrole compound can be the same or different. For example, 2,5-dimethylpyrrole, 2-ethyl-5-methylpyrrole and 2-ethyl-5-propyl pyrrole are among the suitable 2,5-disubstituted pyrroles that can be produced in accordance with this invention. In other embodiments, the groups attached to the 2- and 5-positions of the substituted furan or substituted pyrrole compound can be the same. Generally, the groups attached to the 2- and 5-position of the substituted furan or substituted pyrrole compound can be any furan or pyrrole substituent group disclosed herein. For instance, $R^{2p}$ and $R^{5p}$ independently can be a methyl group, an ethyl group, a n-propyl group, an iso-propyl group, a n-butyl group, a t-butyl group, a phenyl group, a benzyl group, a tolyl group, or a xylyl group.

In a particular non-limiting embodiment, the substituted furan or substituted pyrrole compound can have $C_2$ to $C_{18}$ organyl groups attached at the 2- and 5-positions of the furan or pyrrole ring. In other embodiments, the groups attached at the 2- and 5-positions of the furan or pyrrole ring independently can be $C_2$ to $C_{12}$ organyl groups; or alternatively, $C_2$ to $C_8$ organyl groups. In other particular non-limiting embodiments, the groups attached at the 2- and 5-positions of the furan or pyrrole ring independently can be $C_2$ to $C_{18}$ hydrocarbyl groups; alternatively, $C_2$ to $C_{12}$ hydrocarbyl groups; or alternatively, $C_2$ to $C_8$ hydrocarbyl groups. In yet other particular non-limiting embodiments, the groups attached at the 2- and 5-positions of the furan or pyrrole ring independently can be $C_2$ to $C_{18}$ alkyl groups; alternatively, $C_2$ to $C_{12}$ alkyl groups; or alternatively, $C_2$ to $C_8$ alkyl groups.

In an embodiment, the groups attached to the 2- and 5-positions of the furan or pyrrole ring are attached to the furan or pyrrole ring in such a way that at least one carbon atom attached to the 2- and 5-positions of the furan or pyrrole ring can be a secondary carbon atom; alternatively, the groups attached to the 2- and 5-positions of the furan or pyrrole ring are attached to the furan or pyrrole ring in such a way that both the carbon atoms attached to the 2- and 5-positions of the furan and pyrrole ring are secondary carbon atoms. That is, when the carbon atom of the group attached to the furan or pyrrole ring is a secondary carbon atom, that secondary carbon is attached to one, and only one, other carbon atom besides the carbon atom of the furan or pyrrole ring. In some embodiments, the groups attached to the 2- and 5-positions are attached in such a way that the carbon atoms attached to the 2- and 5-positions of the furan and pyrrole ring are secondary carbon atoms, and at least one of the groups are branched; alternatively, only one of the groups is branched; or alternatively, both of the groups are branched. In other embodiments, the groups attached to the 2- and 5-position of the furan or pyrrole ring can be linear.

In an embodiment wherein the carbon atom of the either of the groups attached to 2- and 5-position of the furan or pyrrole ring is a secondary carbon atom, the groups attached to 2-position and/or the 5-position independently can be an ethyl group, a n-propyl group, a n-butyl group, a n-pentyl group, a n-hexyl group, a n-heptyl group, or a n-octyl group; alternatively, an ethyl group, a n-propyl group, a n-butyl group, or a n-pentyl group; alternatively, an ethyl group; alternatively, a n-propyl group; alternatively, a n-butyl group; alternatively, a n-pentyl group; alternatively, a n-hexyl group; alternatively, a n-heptyl group; or alternatively, a n-octyl group. For example, the pyrrole compound can be a 2,5-disubstituted pyrrole, such as 2,5-diethyl pyrrole.

In another embodiment, $R^{2p}$ and $R^{5p}$ independently can be any group disclosed herein and wherein at least one of the groups attached to the 2- and 5-positions can be attached in a manner wherein the carbon atom attached to the furan or pyrrole ring is a secondary carbon atom, and $R^{3p}$ and $R^{4p}$ independently can be hydrogen or any non-hydrogen furan or pyrrole substituent disclosed herein; alternatively, $R^{2p}$ and $R^{5p}$ independently can be any group disclosed herein, and wherein at least one of the groups attached to the 2- and 5-positions can be attached in a manner wherein the carbon atom attached to the furan or pyrrole ring is a secondary carbon atom, and $R^{3p}$ and $R^{4p}$ are hydrogen. In another embodiment, $R^{2p}$ and $R^{5p}$ independently can be any group disclosed herein, and each of the groups attached to the 2- and 5-positions can be attached in a manner wherein the carbon atom attached to the furan or pyrrole ring can be a secondary carbon atom, and $R^{3p}$ and $R^{4p}$ independently can be hydrogen or any non-hydrogen furan or pyrrole substituent disclosed herein; alternatively, $R^{2p}$ and $R^{5p}$ independently can be any group disclosed herein, wherein the groups attached to the 2- and 5-positions can be attached in a manner wherein the carbon atoms attached to the furan or pyrrole ring can be secondary carbon atoms, and $R^{3p}$ and $R^{4p}$ are hydrogen.

In some non-limiting embodiments wherein the groups attached to the 2- and 5-positions are attached in such a manner that at least one (or alternatively both) of the carbon atoms attached to the pyrrole ring are secondary carbons, the substituted pyrrole compound can be a 2,5-dialkylpyrrole, a 2,3,5-trialkylpyrrole, a 2,4,5-trialkylpyrrole, a 2,3,4,5-tetraalkylpyrrole, or any combination thereof; alternatively, a 2,5-dialkylpyrrole; alternatively, a 2,3,5-trialkylpyrrole; alternatively, a 2,4,5-trialkylpyrrole; or alternatively, a 2,3,4,5-tetraalkylpyrrole.

In some non-limiting embodiments wherein the groups attached to the 2- and 5-positions are attached in such a manner that at least one (or alternatively both) of the carbon atoms attached to the pyrrole ring are secondary carbons, the substituted pyrrole can be 2-methyl-5-ethylpyrrole, 2,5-diethylpyrrole, 2,5-di-n-propylpyrrole, 2,5-di-n-butylpyrrole, 2,5-di-n-pentylpyrrole, 2,5-di-n-hexylpyrrole, 2,5-di-n-heptylpyrrole, 2,5-di-n-octylpyrrole, 2,3,5-triethylpyrrrole, 2,3,5-tri-n-butylpyrrole, 2,3,5-tri-n-pentylpyrrole, 2,3,5-tri-n-hexylpyrrole, 2,3,5-tri-n-heptylpyrrole, 2,3,5-tri-n-octylpyrrole, 2,3,4,5-tetraethylpyrrole, 2,3,4,5-tetra-n-butylpyrrole, 2,3,4,5-tetra-n-hexylpyrrole, 2,5-bis(2',2',2'-trifluoroethyl)pyrrole, 2,5-bis(2'-methoxymethyl)pyrrole, or any combination thereof; alternatively, 2-methyl-5-ethylpyrrole, 2,5-diethylpyrrole, 2,5-di-n-propylpyrrole, 2,5-di-n-butylpyrrole, 2,5-di-n-pentylpyrrole, 2,5-di-n-hexylpyrrole, 2,5-di-n-heptylpyrrole, 2,5-di-n-octylpyrrole, or any combination thereof; alternatively, 2-methyl-5-ethylpyrrole; alternatively, 2,5-diethylpyrrole; alternatively, 2,5-di-n-propylpyrrole; alternatively, 2,5-di-n-butylpyrrole; alternatively, 2,5-di-n-pentylpyrrole; alternatively, 2,5-n-hexylpyrrole; alternatively, 2,5-di-n-heptylpyrrole; or alternatively, 2,5-di-n-octylpyrrole.

In an embodiment, the substituted furan (or substituted pyrrole) compound can have a hydrogen atom located on at least one furan (or pyrrole) ring carbon atom adjacent to the oxygen atom of the furan ring (or nitrogen atom of the pyrrole ring), and a bulky group located on a furan (or pyrrole) ring carbon atom adjacent to any furan (or pyrrole) ring carbon atom bearing the hydrogen atom adjacent to the oxygen atom of the furan ring (or nitrogen atom of the pyrrole ring); alternatively, has a hydrogen atom located on each furan (or each pyrrole) ring carbon atom adjacent to the oxygen atom of the furan ring (or nitrogen atom of the pyrrole ring), and a bulky group located on each furan (or each pyrrole) ring carbon atom adjacent to the furan (or pyrrole) ring carbon atoms bearing the hydrogen atom adjacent to the oxygen atom of the furan ring (or nitrogen atom of the pyrrole ring). Generally, each group in this embodiment can be any group described herein, and have any number of carbons described herein that meets the requirements of the substituted furan or substituted pyrrole compound. For example, any non-hydrogen pyrrole group located on a pyrrole ring carbon atom adjacent to the pyrrole ring nitrogen atom, and any non-hydrogen pyrrole group located on a pyrrole ring carbon atom adjacent to a pyrrole ring carbon atom bearing an non-hydrogen pyrrole group on a pyrrole ring carbon atom adjacent to the pyrrole ring nitrogen atom can be any $C_1$ to $C_{18}$, $C_1$ to $C_{15}$, $C_1$ to $C_{10}$, or $C_1$ to $C_5$ organyl group (alternatively, any hydrocarbyl group) described herein, while the group located on a pyrrole ring carbon atom adjacent to a the pyrrole ring carbon atom bearing the hydrogen atom that is adjacent to the nitrogen atom of the pyrrole ring can be any bulky $C_3$ to $C_{18}$, $C_3$ to $C_{15}$, $C_3$ to $C_{10}$, or $C_3$ to $C_5$ organyl group (alternatively, any hydrocarbyl group) described herein. In an embodiment, each bulky substituent can be a triorganylsilyl group, or alternatively, a trihydrocarbylsilyl group. Generally, the triorganylsilyl and/or the trihydrocarbylsilyl group can have the same number of carbon atoms as the silyl group which can be utilized as a furan or pyrrole substituent described herein. In an embodiment, each bulky substituent can be a trialkylsilyl group, a triphenylsilyl group, or a tri(substituted phenyl)silyl group; alternatively, a trialkylsilyl group; alternatively, a triphenylsilyl group; or alternatively, a tri(substituted phenyl)silyl group.

In an embodiment, the substituted furan compound can be a furan compound having formula F2, formula F3, formula F4, formula F5, or a combination thereof; alternatively, formula F2, formula F3, formula F4, or a combination thereof; alternatively, formula F2; alternatively, formula F3; alternatively, formula F4; or alternatively, formula F5.

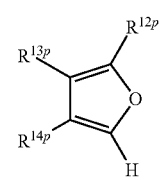

F2

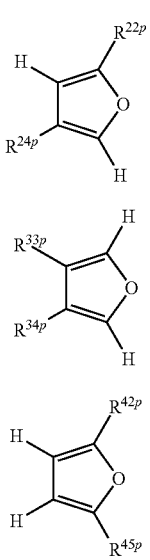

F3

F4

F5

In an embodiment, the substituted pyrrole compound can be a pyrrole compound having formula P2, formula P3, formula P4, formula P5, or a combination thereof; alternatively, formula P2, formula P3, formula P4, or any combination thereof; alternatively, formula P2; alternatively, formula P3; alternatively, formula P4; or alternatively, formula P5.

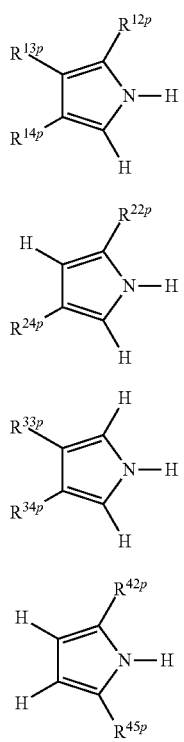

P2

P3

P4

P5

In formulas F2, F3, F4, F5, P2, P3, P4, and P5, $R^{12p}$, $R^{13p}$, $R^{14p}$, $R^{22p}$, $R^{24p}$, $R^{33p}$, $R^{34}$, $R^{42}$, and $R^{45}$ independently can be any $C_1$ to $C_{18}$, $C_1$ to $C_{15}$, $C_1$ to $C_{10}$, or $C_1$ to $C_5$ organyl group described herein; alternatively, any $C_1$ to $C_{18}$, $C_1$ to $C_{15}$, $C_1$ to $C_{10}$, or $C_1$ to $C_5$ hydrocarbyl group described herein; or alternatively, any $C_3$ to $C_{60}$, $C_3$ to $C_{45}$, $C_3$ to $C_{18}$, or $C_3$ to $C_{12}$ silyl group described herein.

In an embodiment, $R^{12p}$, $R^{13p}$, and $R^{22p}$ independently can be any furan or pyrrole substituent group disclosed herein, while $R^{14p}$, $R^{24p}$, $R^{33p}$, and $R^{34p}$ independently can be any bulky furan or pyrrole substituent disclosed herein. The bulky substituent can be any bulky $C_3$ to $C_{18}$, $C_3$ to $C_{15}$, $C_3$ to $C_{10}$, or $C_3$ to $C_5$ organyl group (or alternatively, any hydrocarbyl group) described herein. In an embodiment, each bulky substituent can be any triorganylsilyl group (or alternatively, any trihydrocarbylsilyl group) described herein.

In one embodiment, the bulky furan or pyrrole substituent can be defined as one wherein the carbon atom of the bulky group that is attached to the furan or pyrrole ring carbon atom is a tertiary or quaternary carbon atom, or one wherein the carbon atom of the bulky group that is adjacent to the carbon atom attached to the furan or pyrrole ring carbon atom is a tertiary or quaternary carbon atom. In another embodiment, the bulky furan or pyrrole substituent can be defined as one wherein the carbon atom of bulky group that is attached to the furan or pyrrole ring carbon atom is a tertiary carbon atom, or one wherein the carbon atom of the bulky group that is adjacent to the carbon atom attached to the furan or pyrrole ring carbon atom is a tertiary carbon atom. Yet, in another embodiment, the bulky furan or pyrrole substituent can be defined as one wherein the carbon atom of bulky group that is attached to the furan or pyrrole ring carbon atom is a quaternary carbon atom, or one wherein the carbon atom of the bulky group that is adjacent to the carbon atom attached to the furan or pyrrole ring carbon atom is a quaternary carbon atom. In still another embodiment, a bulky silyl group is one wherein the silicon atom of the bulky silyl group attached to the furan or pyrrole ring carbon is attached to four carbon atoms.

In another embodiment, the bulky furan or pyrrole substituent can be defined as one wherein the carbon atom of the bulky group that is attached to the furan or pyrrole ring carbon atom is attached to 3 or 4 carbon atoms, or one wherein the carbon atom of the bulky group that is adjacent to the carbon atom attached to the furan or pyrrole ring carbon atom is attached to 3 or 4 carbon atoms. In another embodiment, the bulky furan or pyrrole substituent can be defined as one wherein the carbon atom of the bulky group that is attached to the furan or pyrrole ring carbon atom is attached to 3 carbon atoms, or one wherein the carbon atom of the bulky group that is adjacent to the carbon atom attached to the furan or pyrrole ring carbon atom is attached to 3 carbon atoms. Yet, in another embodiment, the bulky furan or pyrrole substituent can be defined as one wherein the carbon atom of the bulky group that is attached to the furan or pyrrole ring carbon atom is attached to 4 carbon atoms, or one wherein the carbon atom of the bulky group that is adjacent to the carbon atom attached to the furan or pyrrole ring carbon atom is attached to 4 carbon atoms.

For illustration purposes, formula E1 identifies the carbon atom attached to the pyrrole ring, and the carbon atom adjacent to the carbon atom attached to the pyrrole ring carbon atom:

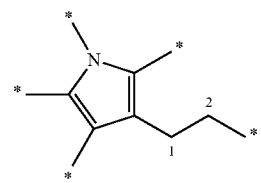

E1

In formula E1, the carbon atom labeled 1 within the group attached to the pyrrole ring represents the carbon atom attached to the pyrrole ring carbon atom. The carbon atom labeled 2 within the group attached to the pyrrole ring represents the carbon atom adjacent to the carbon atom attached to the pyrrole ring carbon atom.

In an embodiment, the bulky substituent independently can be an alkyl group, a substituted alkyl group, a cycloalkyl group, a substituted cycloalkyl group, an aromatic group, a substituted aromatic group, an aryl group, a substituted aryl group, an aralkyl group, a substituted aralkyl group, or a silyl group. Generally, the alkyl group, substituted alkyl group, cycloalkyl group, substituted cycloalkyl group, aromatic group, substituted aromatic group, aryl group, substituted aryl group, aralkyl group, substituted aralkyl group, and/or silyl group which can be utilized as the bulky substituent can have the same number of carbon atoms as the bulky organyl (or hydrocarbyl) furan or pyrrole substituent disclosed herein. Alkyl groups, substituted alkyl groups, cycloalkyl groups, substituted cycloalkyl groups, aromatic groups, substituted aromatic groups, aryl groups, substituted aryl groups, aralkyl groups, substituted aralkyl groups, and silyl groups are generally disclosed herein and those that meet the criteria for a bulky substituent can be utilized, without limitation, to further describe the furan or pyrrole compounds which can be used in embodiments disclosed herein.

In an embodiment, each bulky substituent independently can be a propan-2-yl group, a butan-2-yl, a 2-methylpropan-1-yl group, a 2-methylpropan-2-yl group, a pentan-2-yl group, a pentan-3-yl group, a 2-methylbutan-1-yl group, a 2-methylbutan-2-yl group, a 3-methylbutan-2-yl group, 2,2-dimethylpropan-1-yl group, a hexan-2-yl group, a hexan-3-yl group, a 2-methylpentan-1-yl group, 2-ethylbutan-1-yl group, a 2-methylpentan-2-yl group, a 2,3-dimethylbutan-1-yl group, a 2,3-dimethylbutan-2-yl group, a heptan-2-yl group, a heptan-3-yl group, a heptan-4-yl group, a 2-methylhexan-1-yl group, a 2-ethylpentan-1-yl group, a 2-methylhexan-2-yl group, a 2,3-dimethylpentan-1-yl group, a 2,3-dimethylpentan-2-yl group, a 2,3,3-trimethylpentan-1-yl group, a 2,3,3-trimethylpentan-2-yl group, an octan-2-yl group, an octan-3-yl group, an octan-4-yl group, a 2-methylheptan-1-yl group, a 2-ethylhexan-1-yl group, a 2-methylheptan-2-yl group, a nonan-2-yl group, a nonan-3-yl group, a nonan-4-yl group, a nonan-5-yl group, a decan-2-yl group, a decan-3-yl group, a decan-4-yl group, or a decan-5-yl group. In other embodiments, each bulky substituent independently can be a propan-2-yl group, a butan-2-yl, a 2-methylpropan-1-yl group, a 2-methylpropan-2-yl group, a pentan-2-yl group, a pentan-3-yl group, a 2-methylbutan-1-yl group, a 2-methylbutan-2-yl group, a 3-methylbutan-2-yl group, 2,2-dimethylpropan-1-yl group; alternatively, propan-2-yl group, a 2-methylpropan-2-yl group, or a 2,2-dimethylpropan-1-yl group. In other embodiments, each bulky substituent independently can be a propan-2-yl group; alternatively, a butan-2-yl group; alternatively, a 2-methylpropan-1-yl group; alternatively, a 2-methylpropan-2-yl group; alternatively, a pentan-2-yl group; alternatively, a pentan-3-yl group; alternatively, a 2-methylbutan-1-yl group; alternatively, a 2-methylbutan-2-yl group; alternatively, a 3-methylbutan-2-yl group; or alternatively, a 2,2-dimethylpropan-1-yl group.

In another embodiment, each bulky substituent independently can be a phenyl group or a substituted phenyl group; alternatively, a phenyl group; or alternatively, a substituted phenyl group. For instance, the substituted phenyl group which can be utilized as a bulky substituent can be a 2-methylphenyl group, a 3-methylphenyl group, a 4-methylphenyl group, a 2,3-dimethylphenyl group, a 2,4-dimethylphenyl group, a 2,5-dimethylphenyl group, a 2,6-dimethylphenyl group, a 3,4-dimethylphenyl group, a 3,5-dimethylphenyl group, or a 2,4,6-tripheneyl group. In some embodiments, the substituted phenyl group which can be utilized as a bulky substituent can be a 2-methylphenyl group, a 2,4-dimethylphenyl group, a 2,6-dimethylphenyl group, a 3,5-dimethylphenyl group, or a 2,4,6-tripheneyl group. In other embodiments, the substituted phenyl group which can be utilized as a bulky substituent can be a 2-methylphenyl group; alternatively, a 3-methylphenyl group; alternatively, a 4-methylphenyl group; alternatively, a 2,3-dimethylphenyl group; alternatively, a 2,4-dimethylphenyl group; alternatively, a 2,5-dimethylphenyl group; alternatively, a 2,6-dimethylphenyl group; alternatively, a 3,4-dimethylphenyl group; alternatively, a 3,5-dimethylphenyl group; or alternatively, a 2,4,6-tripheneyl group.

In another embodiment, each bulky substituent independently can be a trimethylsilyl group, a triethylsilyl group, a triisopropylsilyl group, a tri-t-butylsilyl group, or a triphenylsilyl group; alternatively, a trimethylsilyl group, a triethylsilyl group, a triisopropylsilyl group, or a tri-t-butylsilyl group. In certain embodiments, each bulky substituent can be a trimethylsilyl group; alternatively, a triethylsilyl group; alternatively, a triisopropylsilyl group; alternatively, a tri-t-butylsilyl group; or alternatively, a triphenylsilyl group.

As non-limiting examples, the substituted pyrrole compound can be 2-methyl-4-isopropylpyrrole, 2-ethyl-4-isopropylpyrrole, 2-methyl-4-sec-butylpyrrole, 2-ethyl-4-sec-butylpyrrole, 2-methyl-4-isobutylpyrrole, 2-ethyl-4-isobutylpyrrole, 2-methyl-4-t-butylpyrrole, 2-ethyl-4-t-butylpyrrole, 2-methyl-4-neo-pentylpyrrole, or 2-ethyl-4-neopentylpyrrole. In one embodiment, the substituted pyrrole compound can be 2-methyl-4-isopropylpyrrole, 2-ethyl-4-isopropylpyrrole, 2-methyl-4-t-butylpyrrole, 2-ethyl-4-t-butylpyrrole, 2-methyl-4-neo-pentylpyrrole, or 2-ethyl-4-neopentylpyrrole. In another embodiment, the substituted pyrrole compound can be 2-methyl-4-isopropylpyrrole; alternatively, 2-ethyl-4-isopropylpyrrole; alternatively, 2-methyl-4-sec-butylpyrrole; alternatively, 2-ethyl-4-sec-butylpyrrole; alternatively, 2-methyl-4-isobutylpyrrole; alternatively, 2-ethyl-4-isobutylpyrrole; alternatively, 2-methyl-4-t-butylpyrrole; alternatively, 2-ethyl-4-t-butylpyrrole; alternatively, 2-methyl-4-neo-pentylpyrrole; or alternatively, 2-ethyl-4-neopentylpyrrole. In still another embodiment, the substituted pyrrole compound can be 3,4-diisopropylpyrrole, 3,4-di-sec-butylpyrrole, 3,4-diisobutylpyrrole, 3,4-di-t-butylpyrrole, or 3,4-di-neo-pentylpropylpyrrole. Yet, in another embodiment, the substituted pyrrole compound can be 3,4-diisopropylpyrrole; alternatively, 3,4-di-sec-butylpyrrole; alternatively, 3,4-diisobutylpyrrole; alternatively, 3,4-di-t-butylpyrrole; or alternatively, 3,4-di-neo-pentylpropylpyrrole.

Ammonia and Ammonium Salts

Processes for producing a substituted pyrrole compound disclosed herein can employ ammonia, an ammonium salt, or a combination thereof. In some embodiments, ammonia can be contacted with the substituted furan and the catalyst, while in other embodiments, the ammonium salt can be contacted with the substituted furan and the catalyst. Additionally, a combination of ammonia and an ammonium salt (or salts), or a combination of two or more ammonium salts, can be contacted with the substituted furan and the catalyst.

In some embodiments, the ammonia can be anhydrous ammonia or a solution of ammonia in water (also referred to as aqueous ammonia); alternatively, anhydrous ammonia; or alternatively, aqueous ammonia. Generally, anhydrous ammonia refers to ammonia having less that 1000 ppm, 500 ppm, 250 ppm, 125 ppm, 100 ppm, 75 ppm, or 50 ppm water. In an embodiment, the aqueous ammonia can be a solution of 2 wt. % to 50 wt. % ammonia in water. In other embodiments, the aqueous ammonia can be a solution of 4 wt. % to 12 wt. % ammonia in water; alternatively, 8 wt. % to 40 wt. % ammonia in water; alternatively, 9 wt. % to 28 wt. % ammonia in water; or alternatively, 23 wt. % to 35 wt. % ammonia in water.

In some embodiments, an ammonium salt can be utilized. Suitable ammonium salts can include, but are not limited to, an ammonium carboxylate, an ammonium carbonate, an ammonium bicarbonate, ammonium hydroxide, an ammonium halide, an ammonium nitrate, an ammonium nitrite, an ammonium phosphate, an ammonium sulfate, an ammonium sulfite, an ammonium bisulfite, or any combination thereof; ammonium hydroxide, an ammonium halide, an ammonium nitrate, an ammonium phosphate, an ammonium sulfate, or any combination thereof; alternatively, an ammonium carbonate, an ammonium bicarbonate, or any combination thereof; alternatively, an ammonium nitrate, an ammonium phosphate, an ammonium sulfate, or any combination thereof; alternatively, an ammonium carboxylate; alternatively, an ammonium carbonate; alternatively, an ammonium bicarbonate; alternatively, ammonium hydroxide; alternatively, an ammonium halide; alternatively, an ammonium nitrate; alternatively, an ammonium nitrite; alternatively, an ammonium phosphate; alternatively, an ammonium sulfate; alternatively, an ammonium sulfite; or alternatively, an ammonium bisulfite.

In an embodiment, the carboxylate of the ammonium carboxylate can be a $C_1$ to $C_5$ carboxylate; or alternatively, a $C_1$ to $C_2$ carboxylate. In some embodiments, the carboxylate of the ammonium carboxylate can be formate, acetate, oxylate, propionate, citrate, butyrate, tartrate, or any combination thereof; alternatively, formate, acetate, or any combination thereof; alternatively, formate; alternatively, acetate; alternatively, oxylate; or alternatively, citrate. In an embodiment, the halide of an ammonium halide can be fluoride, chloride, bromide, or iodide; alternatively, fluoride; alternatively, chloride; alternatively, bromide; or alternatively, iodide.

In an embodiment, the ammonium salt can comprise ammonium formate, ammonium acetate, ammonium oxylate, ammonium hydrogenoxylate, ammonium citrate, ammonium hydrogen citrate, ammonium carbonate, ammonium bicarbonate, ammonium fluoride, ammonium chloride, ammonium bromide, ammonium iodide, ammonium hydroxide, ammonium nitrate, ammonium nitrite, ammonium phosphate, ammonium hydrogenphosphate, ammonium dihydrogenphosphate, ammonium sulfate, ammonium hydrogensulfate, ammonium sulfite, ammonium bisulfite, or any combination thereof; alternatively, ammonium formate, ammonium acetate, ammonium oxylate, ammonium hydrogenoxylate, ammonium citrate, ammonium hydrogen citrate, or any combination thereof; alternatively, ammonium carbonate, ammonium bicarbonate, or any combination thereof; alternatively, ammonium fluoride, ammonium chloride, ammonium bromide, ammonium iodide, or any combination thereof; alternatively, ammonium nitrate, ammonium nitrite, or any combination thereof; alternatively, ammonium phosphate, ammonium hydrogenphosphate, ammonium dihydrogenphosphate, or any combination thereof; alternatively, ammonium sulfate, ammonium hydrogensulfate, ammonium sulfite, ammonium bisulfite, or any combination thereof; alternatively, ammonium fluoride, ammonium chloride, ammonium bromide, ammonium iodide, ammonium hydroxide, ammonium nitrate, ammonium phosphate, ammonium sulfate, or any combination thereof. For instance, in an embodiment, the ammonium salt can comprise ammonium formate; alternatively, ammonium acetate; alternatively, ammonium citrate; alternatively, ammonium carbonate; alternatively, ammonium bicarbonate; alternatively, ammonium fluoride; alternatively, ammonium chloride; alternatively, ammonium bromide; alternatively, ammonium iodide, alternatively, ammonium hydroxide; alternatively, ammonium nitrate; alternatively, ammonium nitrite; alternatively, ammonium phosphate; alternatively, ammonium hydrogenphosphate; alternatively, ammonium dihydrogenphosphate; alternatively, ammonium sulfate; alternatively, ammonium hydrogensulfate; alternatively, ammonium sulfite; or alternatively, ammonium bisulfite.

In an embodiment, any of the ammonium salts disclosed herein can be hydrated or non-hydrated; alternatively, hydrated; or alternatively, non-hydrated. Generally, a non-hydrated ammonium salt is one which contains less than 10,000 ppm, 5,000 ppm, 2,500 ppm, 1000 ppm, 500 ppm, 250 ppm, 125 ppm, 100 ppm, 75 ppm, or 50 ppm water. In some embodiments, the ammonium salt can be in an aqueous solution.

The ammonium salt, in certain embodiments, can comprise a compound having the formula: $(NH_4)_m X$. In this formula, X is an anion, and m is an integer based on the valence of the anion. For instance, if X is a chloride ion, m will be equal to 1, and the ammonium salt will be ammonium chloride ($NH_4Cl$). In an embodiment, the anion X can be formate, acetate, citrate, carbonate, bicarbonate, chloride, fluoride, bifluoride, bromide, iodide, hydroxide, nitrate, nitrite, phosphate, hydrogenphosphate, dihydrogenphosphate, sulfate, hydrogensulfate, sulfite, bisulfite, fluorosulfate, fluorophosphate, trifluoroacetate, triflate, fluorozirconate, fluorotitanate, phospho-tungstate, tetrafluoroborate, hexafluorosilicate, hexafluorophosphate, or any combination thereof; alternatively, formate, acetate, chloride, fluoride, bifluoride, bromide, iodide, hydroxide, nitrate, phosphate, sulfate, fluorosulfate, fluorophosphate, trifluoroacetate, triflate, tetrafluoroborate, hexafluorosilicate, hexafluorophosphate, or any combination thereof; alternatively, formate, acetate, chloride, fluoride, bifluoride, bromide, iodide, hydroxide, nitrate, phosphate, sulfate, or any combination thereof. In another embodiment, the anion X can be formate; alternatively, acetate; alternatively, citrate; alternatively, carbonate; alternatively, bicarbonate; alternatively, chloride; alternatively, fluoride; alternatively, bifluoride; alternatively, bromide; alternatively, iodide; alternatively, hydroxide; alternatively, nitrate; alternatively, nitrite; alternatively, phosphate; alternatively, hydrogenphosphate; alternatively, dihydrogenphosphate; alternatively, sulfate; alternatively, hydrogensulfate; alternatively, sulfite; alternatively, bisulfite; alternatively, fluorosulfate; alternatively, fluorophosphate; alternatively, trifluoroacetate; alternatively, triflate; alternatively, fluorozirconate; alternatively, fluorotitanate; alternatively, phospho-tungstate; alternatively, tetrafluoroborate; alternatively, hexafluorosilicate; or alternatively, hexafluorophosphate.

Catalysts

Generally, the catalyst employed in the processes for producing a substituted pyrrole compound disclosed herein can comprise (or consist essentially of, or consist of) a solid oxide, a treated solid oxide, a molecular sieve or zeolite, a clay or pillared clay, or an acidic resin, including combinations thereof. For instance, it is contemplated that mixtures or combinations of two or more catalysts can be employed in certain embodiments of the invention.

In accordance with one embodiment, the catalyst can comprise a solid oxide, a treated solid oxide, a molecular sieve or zeolite, or a combination thereof. In another embodiment, the catalyst can comprise a treated solid oxide, a molecular sieve or zeolite, a clay or pillared clay, or a combination thereof. In yet another embodiment, the catalyst can comprise a molecular sieve or zeolite, an acidic resin, or a combination thereof. In still another embodiment, the catalyst can comprise a solid oxide; alternatively, a treated solid oxide; alternatively, a molecular sieve or zeolite; alternatively, a clay or pillared clay; or alternatively, an acidic resin.

Solid Oxides

The catalyst employed in the processes for producing a substituted pyrrole compound can comprise, consist essentially of, or consist of, a solid oxide. Generally, the solid oxide can comprise oxygen and one or more elements selected from Group 2, 3, 4, 5, 6, 7, 8, 9, 10, 11, 12, 13, 14, or 15 of the periodic table, or comprise oxygen and one or more elements selected from the lanthanide or actinide elements (See: Hawley's Condensed Chemical Dictionary, 11$^{th}$ Ed., John Wiley & Sons, 1995; Cotton, F. A., Wilkinson, G., Murillo, C. A., and Bochmann, M., Advanced Inorganic Chemistry, 6$^{th}$ Ed., Wiley-Interscience, 1999). For example, the solid inorganic oxide can comprise oxygen and an element, or elements, selected from Al, B, Be, Bi, Cd, Co, Cr, Cu, Fe, Ga, La, Mn, Mo, Ni, Sb, Si, Sn, Sr, Th, Ti, V, W, P, Y, Zn, and Zr.

Suitable examples of solid oxide materials or compounds that can be used to produce substituted pyrrole compounds can include, but are not limited to, $Al_2O_3$, $B_2O_3$, BeO, $Bi_2O_3$, CdO, $CO_3O_4$, $Cr_2O_3$, CuO, $Fe_2O_3$, $Ga_2O_3$, $La_2O_3$, $Mn_2O_3$, $MoO_3$, NiO, $P_2O_5$, $Sb_2O_5$, $SiO_2$, $SnO_2$, SrO, $ThO_2$, $TiO_2$, $V_2O_5$, $WO_3$, $Y_2O_3$, ZnO, $ZrO_2$, and the like, including mixed oxides thereof, and combinations thereof.

The solid oxide catalyst can encompass oxide materials such as alumina, "mixed oxide" compounds thereof such as silica-alumina, and combinations or mixtures of more than one solid oxide material. Mixed oxides such as silica-alumina can be single or multiple chemical phases with more than one metal combined with oxygen to form the solid oxide. Examples of mixed oxides that can be used in the present invention include, but are not limited to, silica-alumina, silica-coated alumina, silica-titania, silica-zirconia, alumina-titania, alumina-zirconia, zinc-aluminate, alumina-boria, silica-boria, aluminum phosphate, aluminophosphate, aluminophosphate-silica, titania-zirconia, and the like, or a combination thereof. Silica-coated aluminas also can be catalysts for the processes disclosed herein; such oxide materials are described in, for example, U.S. Patent Publication No. 2010-0076167, the disclosure of which is incorporated herein by reference in its entirety.

The percentage of each oxide in a mixed oxide can vary depending upon the respective oxide materials. As an example, a silica-alumina typically has an alumina content from 5 to 95% by weight. According to one embodiment of this invention, the alumina content of the silica-alumina can be from 5 to 50%, or from 8% to 30%, alumina by weight. In another embodiment, high alumina content silica-alumina compounds can be employed, in which the alumina content of these silica-alumina materials typically ranges from 60% to 90%, or from 65% to 80%, alumina by weight.

In one embodiment, the solid oxide catalyst can comprise (or consist essentially of, or consist of) silica-alumina, silica-coated alumina, silica-titania, silica-zirconia, alumina-titania, alumina-zirconia, zinc-aluminate, alumina-boria, silica-boria, aluminum phosphate, aluminophosphate, aluminophosphate-silica, titania-zirconia, or a combination thereof; alternatively, silica-alumina; alternatively, silica-coated alumina; alternatively, silica-titania; alternatively, silica-zirconia; alternatively, alumina-titania; alternatively, alumina-zirconia; alternatively, zinc-aluminate; alternatively, alumina-boria; alternatively, silica-boria; alternatively, aluminum phosphate; alternatively, aluminophosphate; alternatively, aluminophosphate-silica; or alternatively, titania-zirconia.

In another embodiment, the solid oxide can comprise (or consist essentially of, or consist of) silica, alumina, silica-alumina, silica-coated alumina, titania, zirconia, magnesia, boria, zinc oxide, or any combination thereof. For instance, the solid oxide can comprise (or consist essentially of, or consist of) silica, alumina, silica-alumina, silica-coated alumina, or a combination thereof; alternatively, silica-alumina, silica-coated alumina, or a combination thereof; alternatively, silica; alternatively, alumina; alternatively, silica-alumina; alternatively, silica-coated alumina; alternatively, titania; alternatively, zirconia; alternatively, magnesia; alternatively, boria; or alternatively, zinc oxide.

According to an embodiment of the present invention, the solid oxide can have a pore volume greater than 0.1 cc/g, or alternatively, greater than 0.5 cc/g. Often, the solid oxide can have a pore volume greater than 1.0 cc/g. Additionally, or alternatively, the solid oxide can have a surface area greater than 100 m$^2$/g; alternatively, greater than 250 m$^2$/g; or alternatively, greater than 350 m$^2$/g. For example, the solid oxide can have a surface area of from 100 to 1000 m$^2$/g, from 200 to 800 m$^2$/g, or from 250 to 600 m$^2$/g.

Treated Solid Oxides

The catalyst employed in the processes for producing a substituted pyrrole compound can comprise, consist essentially of, or consist of, a treated solid oxide. The solid oxide can be any solid oxide disclosed or described herein. In some embodiments, the treated solid oxide can comprise (or consist essentially of, or consist of) an acid-functionalized solid oxide, a base-functionalized solid oxide, or a combination thereof; alternatively, an acid-functionalized solid oxide; or alternatively, a base-functionalized solid oxide. For example, a mixture or combination of an acid-functionalized solid oxide and a base-functionalized solid oxide can be employed, or a solid oxide that has been both acid-functionalized and base-functionalized can be employed. In another embodiment, the treated solid oxide can comprise (or consist essentially of, or consist of) a solid oxide that has been treated to increase its hydrophobicity. Such hydrophobic-treated solid oxides also can be acid-functionalized or base-functionalized prior to, during, or after the treatment to increase the material's hydrophobicity. In an embodiment, the treated solid oxide can comprise (or consist essentially of, or consist of) an acid-functionalized solid oxide, a base-functionalized solid oxide, a hydrophobic-functionalized solid oxide, or a combination thereof.

In some embodiments, the treated solid oxide can comprise (or consist essentially of, or consist of) a solid oxide treated with an electron-withdrawing anion. While not intending to be bound by the following statement, it is believed that treatment of the solid oxide with an electron-withdrawing component augments or enhances the acidity of the oxide. Thus, either the treated solid oxide exhibits Lewis or Brønsted acidity that is typically greater than the Lewis or Brønsted acid strength of the untreated solid oxide, or the treated solid oxide has a greater number of acid sites than the untreated solid oxide, or both.

The electron-withdrawing component used to treat the solid oxide can be any component that increases the Lewis or Brønsted acidity of the solid oxide upon treatment (as compared to the solid oxide that is not treated with the electron-withdrawing anion). According to an embodiment of the present invention, the electron-withdrawing component can be an electron-withdrawing anion derived from a salt, an acid, or other compound, such as a volatile organic compound, that serves as a source or precursor for that anion. Examples of electron-withdrawing anions include, but are not limited to, sulfate, bisulfate, fluoride, chloride, bromide, iodide, fluorosulfate, fluoroborate, phosphate, fluorophosphate, trifluoroacetate, triflate, fluorozirconate, fluorotitanate, phosphotungstate, and the like, including mixtures and combinations thereof. In addition, other ionic or non-ionic compounds that serve as sources for these electron-withdrawing anions also can be employed in the present invention.

It is contemplated, in embodiments of the invention, that the electron-withdrawing anion can comprise (or consist essentially of, or consist of) sulfate, bisulfate, fluoride, chloride, bromide, iodide, fluorosulfate, fluoroborate, phosphate, fluorophosphate, trifluoroacetate, triflate, fluorozirconate, fluorotitanate, phospho-tungstate, or any combination thereof. For instance, the electron-withdrawing anion can comprise fluoride, fluorosulfate, fluoroborate, fluorophosphate, trifluoroacetate, triflate, fluorozirconate, fluorotitanate, or a combination thereof; alternatively, sulfate, bisulfate, triflate, fluoride, chloride, bromide, iodide, or a combination thereof; alternatively, fluoride, chloride, bromide, iodide, or a combination thereof; alternatively, sulfate; alternatively, bisulfate; alternatively, fluoride; alternatively, chloride; alternatively, bromide; alternatively, iodide; alternatively, fluorosulfate; alternatively, fluoroborate (also referred to as tetrafluoroborate); alternatively, phosphate; alternatively, fluorophosphate; alternatively, trifluoroacetate; alternatively, triflate; alternatively, fluorozirconate; alternatively, fluorotitanate; or alternatively, phosphotungstate.

In another embodiment, the treated solid oxide can comprise (or consist essentially of, or consist of) fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided silica-coated alumina, sulfated silica-coated alumina, phosphated silica-coated alumina, and the like, or combinations thereof. In some embodiments, the treated solid oxide can comprise (or consist essentially of, or consist of) fluorided alumina, chlorided alumina, sulfated alumina, fluorided silica-alumina, chlorided silica-alumina, sulfated silica-alumina, or a combination thereof; alternatively, fluorided silica-coated alumina, sulfated silica-coated alumina, phosphated silica-coated alumina, or a combination thereof; alternatively, fluorided alumina; alternatively, chlorided alumina; alternatively, sulfated alumina; alternatively, fluorided silica-alumina; alternatively, sulfated silica-alumina; alternatively, fluorided silica-zirconia; alternatively, chlorided silica-zirconia; or alternatively, fluorided silica-coated alumina.

When the electron-withdrawing component comprises a salt of an electron-withdrawing anion, the counterion or cation of that salt can be selected from any cation that allows the salt to revert or decompose back to the acid during calcining. Factors that dictate the suitability of the particular salt to serve as a source for the electron-withdrawing anion include, but are not limited to, the solubility of the salt in the desired solvent, the lack of adverse reactivity of the cation, ion-pairing effects between the cation and anion, hygroscopic properties imparted to the salt by the cation, and the like, and thermal stability of the anion. Examples of suitable cations in the salt of the electron-withdrawing anion include, but are not limited to, ammonium, trialkyl ammonium, tetraalkyl ammonium, tetraalkyl phosphonium, $H^+$, $[H(OEt_2)_2]^+$, and the like.

Further, combinations of one or more different electron-withdrawing anions, in varying proportions, can be used to tailor the specific acidity of the treated solid oxide to the desired level. Combinations of electron-withdrawing components can be contacted with the oxide material simultaneously or individually, and in any order that affords the desired treated solid oxide acidity. For example, one embodiment of this invention can employ two or more electron-withdrawing anion source compounds in two or more separate contacting steps.

Thus, one example of such a process by which a treated solid oxide can be prepared is as follows: a selected solid oxide, or combination of solid oxides, is contacted with a first electron-withdrawing anion source compound to form a first mixture; this first mixture is calcined and then contacted with a second electron-withdrawing anion source compound to form a second mixture; the second mixture is then calcined to form a treated solid oxide. In such a process, the first and second electron-withdrawing anion source compounds can be either the same or different compounds.

Various processes can be used to form the treated solid oxide useful in the present invention. The treated solid oxide can comprise the contact product of one or more solid oxides with one or more electron-withdrawing anion sources. It is not required that the solid oxide be calcined prior to contacting the electron-withdrawing anion source. The contact product typically is calcined either during or after the solid oxide is contacted with the electron-withdrawing anion source. The solid oxide can be calcined or uncalcined. Various processes to prepare treated solid oxides that can be employed in this invention have been reported, for example, in U.S. Pat. Nos. 6,107,230, 6,165,929, 6,294,494, 6,300,271, 6,316,553, 6,355,594, 6,376,415, 6,388,017, 6,391,816, 6,395,666, 6,524,987, 6,548,441, 6,548,442, 6,576,583, 6,613,712, 6,632,894, 6,667,274, and 6,750,302, the disclosures of which are incorporated herein by reference in their entirety.

The method by which the oxide can be contacted with the electron-withdrawing component, typically a salt or an acid of an electron-withdrawing anion, can include, but is not limited to, gelling, co-gelling, impregnation of one compound onto another, and the like. Thus, following any contacting method, the contacted mixture of the solid oxide and electron-withdrawing anion can be calcined.

The treated solid oxide can be produced by a process comprising:

1) contacting a solid oxide (or solid oxides) with an electron-withdrawing anion source compound (or compounds) to form a first mixture; and 2) calcining the first mixture to form the treated solid oxide.

In another embodiment, the treated solid oxide can be produced by a process comprising:

1) contacting a solid oxide (or solid oxides) with a first electron-withdrawing anion source compound to form a first mixture;

2) calcining the first mixture to produce a calcined first mixture;

3) contacting the calcined first mixture with a second electron-withdrawing anion source compound to form a second mixture; and 4) calcining the second mixture to form the treated solid oxide.

Calcining of the treated solid oxide generally can be conducted in an ambient atmosphere. In some embodiments, the calcining of the treated solid oxide can be conducted in a dry ambient atmosphere. Calcining can be conducted at a temperature of from 200° C. to 900° C., or alternatively, at a temperature from 300° C. to 800° C., or alternatively, at a temperature of from 400° C. to 700° C. Calcining can be conducted for a time of from 1 minute to 100 hours, or from 30 minutes to 50 hours, or from 1 hour to 15 hours. Thus, for example, calcining can be carried out for 1 to 10 hours at a temperature of from 350° C. to 550° C. Any suitable ambient atmosphere can be employed during calcining Generally, calcining can be conducted in an oxidizing atmosphere, such as air. Alternatively, an inert atmosphere, such as nitrogen or argon, or a reducing atmosphere, such as hydrogen or carbon monoxide, can be used.

In an embodiment, the solid oxide material can be treated with a source of halide ion, sulfate ion, or a combination of anions, and then calcined to provide the treated solid oxide in the form of a particulate solid. For example, the solid oxide material can be treated with a source of sulfate (termed a "sulfating agent"), a source of chloride ion (termed a "chloriding agent"), a source of fluoride ion (termed a "fluoriding agent"), or a combination thereof, and calcined to provide the treated solid oxide catalyst.

The treated solid oxide can comprise (or consist essentially of, or consist of) a fluorided solid oxide in the form of a particulate solid. The fluorided solid oxide can be formed by contacting a solid oxide with a fluoriding agent. The fluoride ion can be added to the oxide by forming a slurry of the oxide in a suitable solvent such as alcohol or water including, but not limited to, the one to three carbon alcohols because of their volatility and low surface tension. Examples of suitable fluoriding agents include, but are not limited to, hydrofluoric acid (HF), ammonium fluoride ($NH_4F$), ammonium bifluoride ($NH_4HF_2$), ammonium tetrafluoroborate ($NH_4BF_4$), ammonium silicofluoride (hexafluorosilicate) (($NH_4)_2SiF_6$), ammonium hexafluorophosphate ($NH_4PF_6$), hexafluorotitanic acid ($H_2TiF_6$), ammonium hexafluorotitanic acid (($NH_4)_2TiF_6$), hexafluorozirconic acid ($H_2ZrF_6$), $AlF_3$, $NH_4AlF_4$, analogs thereof, and combinations thereof. Triflic acid and ammonium triflate also can be employed. For example, ammonium bifluoride ($NH_4HF_2$) can be used as the fluoriding agent, due to its ease of use and availability.

If desired, the solid oxide can treated with a fluoriding agent during the calcining step. Any fluoriding agent capable of thoroughly contacting the solid oxide during the calcining step can be used. For example, in addition to those fluoriding agents described previously, volatile organic fluoriding agents can be used. Examples of volatile organic fluoriding agents useful in this embodiment of the invention include, but are not limited to, freons, perfluorohexane, perfluorobenzene, fluoromethane, trifluoroethanol, and the like, and combinations thereof. Calcining temperatures generally must be high enough to decompose the compound and release fluoride. Gaseous hydrogen fluoride (HF) or fluorine ($F_2$) itself also can be used with the solid oxide if fluorided while calcining Silicon tetrafluoride ($SiF_4$) and compounds containing tetrafluoroborate ($BF_4^-$) also can be employed. One convenient method of contacting the solid oxide with the fluoriding agent is to vaporize a fluoriding agent into a gas stream used to fluidize the solid oxide during calcination.

Similarly, in another embodiment of this invention, the treated solid oxide can comprise (or consist essentially of, or consist of) a chlorided solid oxide in the form of a particulate solid. The chlorided solid oxide can be formed by contacting a solid oxide with a chloriding agent. The chloride ion can be added to the oxide by forming a slurry of the oxide in a suitable solvent. The solid oxide can be treated with a chloriding agent during the calcining step. Any chloriding agent capable of serving as a source of chloride and thoroughly contacting the oxide during the calcining step can be used, such as $SiCl_4$, $SiMe_2Cl_2$, $TiCl_4$, $BCl_3$, and the like, including mixtures thereof. Volatile organic chloriding agents can be used. Examples of suitable volatile organic chloriding agents include, but are not limited to, certain freons, perchlorobenzene, chloromethane, dichloromethane, chloroform, carbon tetrachloride, trichloroethanol, and the like, or any combination thereof. Gaseous hydrogen chloride or chlorine itself also can be used with the solid oxide during calcining. One convenient method of contacting the oxide with the chloriding agent is to vaporize a chloriding agent into a gas stream used to fluidize the solid oxide during calcination.

The amount of fluoride or chloride ion present before calcining the solid oxide generally can be from 1 to 50% by weight, where the weight percent is based on the weight of the solid oxide, for example, silica-alumina, before calcining. According to another embodiment, the amount of fluoride or chloride ion present before calcining the solid oxide can be from 1 to 25% by weight, and according to another embodiment, from 2 to 20% by weight. According to yet another embodiment, the amount of fluoride or chloride ion present before calcining the solid oxide is from 4 to 10% by weight. Once impregnated with halide, the halided oxide can be dried by any suitable method including, but not limited to, suction filtration followed by evaporation, drying under vacuum, spray drying, and the like, although it is also possible to initiate the calcining step immediately without drying the impregnated solid oxide.

In yet another embodiment of this invention, the treated solid oxide can comprise (or consist essentially of, or consist of) a sulfated solid oxide in the form of a particulate solid. In one embodiment, the sulfated solid oxide can comprise sulfate and alumina. In some instances, the sulfated alumina can be formed by a process wherein the alumina is treated with a sulfate source, for example, sulfuric acid or a sulfate salt such as ammonium sulfate. This process can be performed by forming a slurry of the alumina in a suitable solvent, such as alcohol or water, in which the desired concentration of the sulfating agent has been added. Suitable organic solvents include, but are not limited to, the one to three carbon alcohols because of their volatility and low surface tension.

In an embodiment, the amount of sulfate ion present before calcining can be from 0.5 to 100 parts by weight sulfate ion to 100 parts by weight solid oxide. In another embodiment, the amount of sulfate ion present before calcining can be from 1 to 50 parts by weight sulfate ion to 100 parts by weight solid oxide, and according to still another embodiment, from 5 to 30 parts by weight sulfate ion to 100 parts by weight solid oxide. These weight ratios are based on the weight of the solid oxide before calcining. Once impregnated with sulfate, the sulfated oxide can be dried by any suitable method including, but not limited to, suction filtration followed by evaporation, drying under vacuum, spray drying, and the like, although it is also possible to initiate the calcining step immediately.

Molecular Sieves and Zeolites

The catalyst employed in the processes for producing a substituted pyrrole compound can comprise, consist essentially of, or consist of, a molecular sieve or zeolite, including combinations of two or more molecular sieves and/or zeolites. Generally, a zeolite is considered to be an aluminosilicate material, while a molecular sieve is generally considered to be a broader term, which can include an aluminosilicate, an aluminophosphate, a silicoaluminophosphate, and other like materials. Materials of these types are generally and collectively referred to in this disclosure "molecular sieves or zeolites." Molecular sieve or zeolite materials disclosed in the following publications, each of which is incorporated herein by reference in its entirety, are also considered to be within the scope of the "molecular sieves or zeolites" of this invention: "A Review of Zeolite-Like Porous Materials," *Microporous and Mesoporous Materials*, 37 (2000), 243-252; "Zeolite and Molecular Sieve Synthesis," *Chem. Mater.*, 1992, 4, 756-768;

"Zeolites and Molecular Sieves: Not Just Ordinary Catalysts," *Ind. Eng. Chem. Res.,* 1991, 30, 1675-1683; "Atlas of Zeolite Structure Types," *Structure Commission of the International Zeolite Association*, Butterworth & Co., 1987, 1-11; and "Hydrothermal Chemistry of Zeolites," *Academic Press,* 1982, 1-43.

In some embodiments, the molecular sieve or zeolite can comprise (or consist essentially of, or consist of) a Y-zeolite, X-zeolite, USY-zeolite, ZSM, MCM, SSZ, SAPO, ALPO, or any combination thereof, while in other embodiments, the molecular sieve or zeolite can comprise (or consist essentially of, or consist of) a Y-zeolite; alternatively, a X-zeolite; alternatively, a USY-zeolite; alternatively, a ZSM; alternatively, a MCM; alternatively, a SSZ; alternatively, a SAPO; or alternatively, an ALPO. Yet, in another embodiment, the molecular sieve or zeolite can comprise (or consist essentially of, or consist of) LZY-54, ZSM-5, MCM-41, MCM-22, HZSM-5, H-BEA, HY, Fe-substituted LTL, ITQ-6, delaminated zeolite, ITQ-2 delaminated zeolite, or any combination thereof. Further, in some embodiments, the molecular sieve or zeolite can comprise (or consist essentially of, or consist of) LZY-54; alternatively, ZSM-5; alternatively, MCM-41; alternatively, MCM-22; alternatively, HZSM-5; alternatively, H-BEA; alternatively, HY; alternatively, Fe-substituted LTL; alternatively, ITQ-6; alternatively, delaminated zeolite; or alternatively, ITQ-2 delaminated zeolite.

Clays and Pillared Clays

The catalyst employed in the processes for producing a substituted pyrrole compound can comprise, consist essentially of, or consist of, a clay or pillared clay. Optionally, the clay or pillared clay can be acid-functionalized, base-functionalized, treated to increase its hydrophobicity, or combination of such treatments. For instance, the clay or pillared clay optionally can be treated with fluoride, chloride, sulfate, etc., or combinations of various electron-withdrawing anions.

The clay or pillared clay materials that can be employed as catalysts in the disclosed processes can encompass clay materials either in their natural state or that have been treated with various ions by wetting, ion exchange, pillaring, or other process. In some embodiments, the clay or pillared clay material can comprise (or consist essentially of, or consist of) clays that have been ion exchanged with large cations, including polynuclear, highly charged metal complex cations. In other embodiments, the clay or pillared clay material can comprise (or consist essentially of, or consist of) clays that have been ion exchanged with simple salts, including, but not limited to, salts of Al(III), Fe(II), Fe(III), and Zn(II) with ligands such as halide, acetate, sulfate, nitrate, nitrite, and the like.

In another embodiment, the clay or pillared clay material can comprise (or consist essentially of, or consist of) a pillared clay. The term "pillared clay" can be used to refer to clay materials that have been ion exchanged with large, typically polynuclear, highly charged metal complex cations. Examples of such ions include, but are not limited to, Keggin ions which can have charges such as 7+, various polyoxometallates, and other large ions. Thus, the term pillaring generally refers to a simple exchange reaction in which the exchangeable cations of a clay material can be replaced with large, highly charged ions, such as Keggin ions. These polymeric cations are then immobilized within the interlayers of the clay, and when calcined can be converted to metal oxide "pillars," effectively supporting the clay layers as column-like structures. Thus, once the clay has been dried and calcined to produce the supporting pillars between clay layers, the expanded lattice structure can be maintained and the porosity can be enhanced. The resulting pores can vary in shape and size as a function of the pillaring material and the parent clay material used, among other variables. Examples of pillaring and pillared clays are found in: T. J. Pinnavaia, *Science* 220 (4595), 365-371 (1983); J. M. Thomas, Intercalation Chemistry, (S. Whittington and A. Jacobson, eds.) Ch. 3, pp. 55-99, Academic Press, Inc., (1972); U.S. Pat. Nos. 4,452,910; 5,376,611; and 4,060,480; the disclosures of which are incorporated herein by reference in their entirety.

In some embodiments, the clay or pillared clay can comprise (or consist essentially of, or consist of) montmorillonite, bentonite, nontronite, hectorite, laponite, halloysite, vermiculite, mica, fluoromica, chlorite, sepiolite, attapulgite, palygorskite, illite, saponite, allophone, smectite, and the like, or any combination thereof. Suitable clay materials for pillaring can include, but are not limited to, allophanes; smectites, both dioctahedral (Al) and tri-octahedral (Mg) and derivatives thereof such as montmorillonites (bentonites), nontronites, hectorites, or laponites; halloysites; vermiculites; micas; fluoromicas; chlorites; mixed-layer clays; fibrous clays such as sepiolites, attapulgites, and palygorskites; a serpentine clay; illite; laponite; saponite; and the like, or combinations thereof. In one embodiment, the clay or pillared clay can comprise bentonite, montmorillonite, or a combination thereof; alternatively, bentonite; or alternatively, montmorillonite.

Pillared clays can be pretreated, if desired. For example, a pillared bentonite can be pretreated by drying at 300° C. under an inert atmosphere (e.g., dry nitrogen) for 3 hours, before being contacted with a substituted furan and ammonia and/or an ammonium to produce a substituted pyrrole.

Acidic Resins

The catalyst employed in the processes for producing a substituted pyrrole compound can comprise, consist essentially of, or consist of, an acidic resin. Non-limiting examples of acidic resins can include, but are not limited to, styrene-divinylbenzene resins, 4-vinylpyridine divinylbenzene resins, ionomer resins, tetrafluoroethylene resins modified with perfluorovinyl ether groups terminated with sulfonate groups, and the like, including combinations thereof. In some embodiments, the acidic resin can comprise (or consist essentially of, or consist of) an AMBERLYST® catalyst resin, a NAFION® catalyst resin, or a combination thereof; alternatively, an AMBERLYST® catalyst resin; or alternatively, a NAFION® catalyst resin.

Organic Solvents

As described above, the substituted pyrrole compound can be produced in the presence of an organic solvent. The solvent can comprise, consist essentially of, or consist of, a hydrocarbon, an aromatic hydrocarbon, an alcohol, or combinations thereof; alternatively, a hydrocarbon, an aromatic hydrocarbon, or combinations thereof; alternatively, a hydrocarbon; or alternatively, an aromatic hydrocarbon. Hence, mixtures and/or combinations of solvents can be utilized in the processes for synthesizing substituted pyrroles disclosed herein.

In an embodiment, the solvent employed in producing the substituted pyrrole can comprise, consist essentially of, or consist of, a hydrocarbon solvent. Suitable hydrocarbon solvents can include, for example, aliphatic hydrocarbons, petroleum distillates, and the like, or combinations thereof; alternatively, aliphatic hydrocarbons; or alternatively, petroleum distillates. Aliphatic hydrocarbons which can be useful as the solvent include $C_3$ to $C_{20}$ aliphatic hydrocarbons; alternatively, $C_4$ to $C_{15}$ aliphatic hydrocarbons; or alternatively, $C_5$ to $C_{10}$ aliphatic hydrocarbons. The aliphatic hydrocarbons can be cyclic or acyclic and/or can be linear or branched, unless otherwise specified.

Non-limiting examples of suitable acyclic aliphatic hydrocarbon solvents that can be utilized singly or in any combination include pentane (n-pentane or a mixture of linear and branched $C_5$ acyclic aliphatic hydrocarbons), hexane (n-hexane or mixture of linear and branched $C_6$ acyclic aliphatic hydrocarbons), heptane (n-heptane or mixture of linear and branched $C_7$ acyclic aliphatic hydrocarbons), octane (n-octane or a mixture of linear and branched $C_8$ acyclic aliphatic hydrocarbons), decane (n-decane or a mixture of linear and branched $C_{10}$ acyclic aliphatic hydrocarbons), and combinations thereof; alternatively, pentane (n-pentane or a mixture of linear and branched $C_5$ acyclic aliphatic hydrocarbons), hexane (n-hexane or mixture of linear and branched $C_6$ acyclic aliphatic hydrocarbons), heptane (n-heptane or mixture of linear and branched $C_7$ acyclic aliphatic hydrocarbons), octane (n-octane or a mixture of linear and branched $C_8$ acyclic aliphatic hydrocarbons), and combinations thereof; alternatively, hexane (n-hexane or a mixture of linear and branched $C_6$ acyclic aliphatic hydrocarbons), heptane (n-heptane or mixture of linear and branched $C_7$ acyclic aliphatic hydrocarbons), octane (n-octane or a mixture of linear and branched $C_8$ acyclic aliphatic hydrocarbons), and combinations thereof; alternatively, pentane (n-pentane or a mixture of linear and branched $C_5$ acyclic aliphatic hydrocarbons); alternatively, hexane (n-hexane or mixture of linear and branched $C_6$ acyclic aliphatic hydrocarbons); alternatively, heptane (n-heptane or mixture of linear and branched $C_7$ acyclic aliphatic hydrocarbons); or alternatively, octane (n-octane or a mixture of linear and branched $C_8$ acyclic aliphatic hydrocarbons).

Non-limiting examples of suitable cyclic aliphatic hydrocarbon solvents include, but are not limited to, cyclohexane, methyl cyclohexane, and the like, or combinations thereof; alternatively cyclohexane; or alternatively, methylcyclohexane.

In an embodiment, the solvent employed in producing the substituted pyrrole can comprise, consist essentially of, or consist of, an aromatic hydrocarbon solvent. Aromatic hydrocarbons which can be useful as a solvent include $C_6$ to $C_{30}$ aromatic hydrocarbons; alternatively, $C_6$ to $C_{20}$ aromatic hydrocarbons; or alternatively, $C_6$ to $C_{10}$ aromatic hydrocarbons. Non-limiting examples of suitable aromatic hydrocarbons that can be utilized singly or in any combination include benzene, toluene, xylene (including ortho-xylene, meta-xylene, para-xylene, or mixtures thereof), and ethylbenzene, or combinations thereof; alternatively, benzene; alternatively, toluene; alternatively, xylene (including ortho-xylene, meta-xylene, para-xylene or mixtures thereof); or alternatively, ethylbenzene.

In an embodiment, the solvent employed in producing the substituted pyrrole can comprise, consist essentially of, or consist of, an alcohol solvent such as, for example, a $C_2$ to $C_{20}$ alcohol; alternatively, a $C_2$ to $C_{10}$ alcohol; or alternatively, a $C_2$ to $C_5$ alcohol. Non-limiting examples of suitable alcohols which can be utilized as a solvent include methanol, ethanol, propanol, isopropanol, n-butanol, isobutanol, pentanol, hexanol, heptanol, octanol, benzyl alcohol, phenol, cyclohexanol, and the like, or combinations thereof.

EXAMPLES

The invention is further illustrated by the following examples, which are not to be construed in any way as imposing limitations to the scope of this invention. Various other aspects, embodiments, modifications, and equivalents thereof which, after reading the description herein, may suggest themselves to one of ordinary skill in the art without departing from the spirit of the present invention or the scope of the appended claims.

Examples 1-11

Synthesis of 2,5-dimethylpyrrole from 2,5-dimethylfuran

The synthesis of 2,5-dimethylpyrrole from 2,5-dimethylfuran in Examples 1-11 was performed in accordance with the following procedure. A stainless steel reaction tube capped at one end was charged with a solid catalyst, 2,5-dimethylfuran, and an ammonium hydroxide solution (28% in $H_2O$). The reaction tube was purged for 5 min with dry nitrogen gas and capped. The reaction tube was then placed in a pre-heated oven at the desired reaction temperature, and the mixture was allowed to react for the desired reaction time. The reaction pressure for Examples 1-11 was in the range of 1000 to 2500 psig. After removing the reaction tube from the oven, the tube and its reaction product were cooled to ambient temperature, followed by depressurization. The reaction product was decanted into a 20-mL glass vial. The reaction tube was rinsed with 3-5 mL of methylene chloride, and the rinsed mixture was added to the 20-mL vial. The bi-phasic reaction product was then shaken and the phases were allowed to separate. A small sample of the organic fraction was analyzed by GC-FID. GC-FID analysis was performed on a HP 6890 instrument, with an Agilent® 19091-60312 HP-1 methyl siloxane 12 m×200 μm×0.33 μm column, and a FID at 250° C. The injection temperature was 35° C., the oven temperature was 35 to 175° C., and the ramp rate was 1.5° C./min (from 25-85° C.) and 10° C./min (from 85-175° C.). Both 2,5-dimethylfuran and 2,5-dimethylpyrrole were identified by comparing retention times of a separate GC-FID analysis of a standard sample of 2,5-dimethylfuran and 2,5-dimethylpyrrole in methylene chloride. By-products included reaction products having retention times less than 2,5-dimethylpyrrole, as well as "heavies," which had retention times longer than 2,5-dimethylpyrrole.

Table I summarizes certain process conditions and analytical results for Examples 1-11. The weight percent of the catalyst was based on the weight of materials charged to the reaction tube. The product composition information based upon GC-FID data in Table I is presented in weight percentages, unless otherwise specified. The neutral alumina in Examples 3-4 was Sigma-Aldrich Catalog #199974 alumina activated, acidic Brockmann I standard grade, ~150 mesh, 58 Å, surface area of 155 m²/g, and a pH in water of 7.0±0.5. The acidic alumina in Examples 6-7 was Sigma-Aldrich Catalog #199966 alumina activated, acidic Brockmann I standard grade, ~150 mesh, 58 Å, surface area of 155 m²/g, and a pH in water of 4.5±0.5. The F-24 catalyst in Example 8 was acidified clay Grade F-24, manufactured by Engelhard in March 1996. The LZY-54 catalyst in Examples 9-11 was a NaY zeolite, manufactured by UOP under the Molsiv® Absorbents brand as 1/16" clay extrudates bound.

TABLE I

Synthesis of 2,5-dimethylpyrrole from 2,5-dimethylfuran - Examples 1-11

| | | Reactants | | | Reaction Conditions | | Products | |
|---|---|---|---|---|---|---|---|---|
| | | Catalyst | 2,5-Dimethyl- | 28% Aqueous | | | 2,5-Dimethyl- | |
| Example | Catalyst | Amount (wt %) | furan (mL) | ammonia (mL) | Temp. (° C.) | Time (hr) | pyrrole (wt %) | By-products (wt %) |
| 1 | FeCl$_3$(THF)$_3$ | 5 | 1.50 | 1.60 | 160 | 72 | 0.5 | 1 |
| 2 | Ni(acetate)$_2$(H$_2$O)$_4$ | 5 | 1.50 | 1.60 | 150 | 18 | 0 | 0 |
| 3 | Neutral alumina | 5 | 1.50 | 1.60 | 160 | 72 | trace | trace |
| 4 | Neutral alumina | 8 | 0.50 | 0.53 | 350 | 4 | 6 | 2 |
| 5 | Acidic alumina | 8 | 0.50 | 0.53 | 350 | 4 | 12 | 5 |
| 6 | Acidic alumina | 16 | 0.50 | 0.53 | 350 | 4 | 14 | 14 |
| 7 | Acidic alumina | 8 | 0.50 | 0.53 | 350 | 20 | 17 | 30 |
| 8 | Engelhard F-24 | 8 | 0.50 | 0.53 | 350 | 4 | 16 | 12 |
| 9 | LZY-54 | 8 | 0.50 | 0.53 | 350 | 4 | 15 | 15 |
| 10 | LZY-54 | 50 | 0.25 | 0.53 | 350 | 4 | 21 | 7 |
| 11 | LZY-54 | 4 | 0.25 | 0.50 | 300 | 4 | 8 | 2 |

Constructive Examples 12-13

Constructive synthesis of 2,5-dimethylpyrrole from 2,5-dimethylfuran using a fluorided silica-alumina (treated solid oxide)

A silica-alumina (solid oxide) containing about 13% alumina by weight and having a surface area of about 400 m$^2$/g and a pore volume of about 1.2 mL/g can be used as the starting material. Approximately 100 grams of this material is impregnated with a solution containing about 200 mL of water and about 10 grams of ammonium hydrogen fluoride. This mixture is placed in a flat pan and allowed to dry under vacuum at approximately 110° C. for about 12-16 hours.

To calcine the treated solid oxide, about 10 g of the powdered mixture can be placed in a quartz tube fitted with a sintered quartz disk at the bottom. While the powder is supported on the disk, air (or nitrogen) is blown upward through the disk at a linear rate of about 1.6 to 1.8 standard cubic feet per hour. An electric furnace around the quartz tube can be used to control the temperature at a calcining temperature in the 400-600° C. range. The powder is fluidized for about 3 hr in the dry air (or nitrogen). The resultant fluorided silica-alumina is stored under dry nitrogen, and used without exposure to the atmosphere prior to being used as a catalyst.

Constructive Example 12 can be conducted in substantially the same manner as Example 10, with the LZY-54 catalyst replaced by the fluorided silica-alumina. Constructive Example 13 can be conducted in substantially the same manner as Example 11, with the LZY-54 catalyst replaced by the fluorided silica-alumina.

Constructive Examples 14-15

Constructive synthesis of 2,5-dimethylpyrrole from 2,5-dimethylfuran using a sulfated alumina (treated solid oxide)

An alumina (solid oxide) having a surface area of about 300 m$^2$/g and a pore volume of about 1.3 mL/g can be used as the starting material. Approximately 100 g of this material is impregnated with an aqueous solution of ammonium sulfate to equal about 15% sulfate. This mixture is placed in a flat pan and allowed to dry under vacuum at approximately 110° C. for about 12-16 hours.

To calcine the treated solid oxide, about 10 g of the powdered mixture can be placed in a quartz tube fitted with a sintered quartz disk at the bottom. While the powder is supported on the disk, air (or nitrogen) is blown upward through the disk at a linear rate of about 1.6 to 1.8 standard cubic feet per hour. An electric furnace around the quartz tube can be used to control the temperature at a calcining temperature in the 400-600° C. range. The powder is fluidized for about 3 hr in the dry air (or nitrogen). The resultant sulfated alumina can be stored under dry nitrogen, and used without exposure to the atmosphere prior to being used as a catalyst.

Constructive Example 14 can be conducted in substantially the same manner as Example 10, with the LZY-54 catalyst replaced by the sulfated alumina. Constructive Example 15 can be conducted in substantially the same manner as Example 11, with the LZY-54 catalyst replaced by the sulfated alumina.

Constructive Examples 16-17

Constructive synthesis of 2,5-dimethylpyrrole from 2,5-dimethylfuran using a aluminum phosphate catalyst The aluminum phosphate catalyst can be produced as disclosed in *Top. Catal.*, (2010) 53, 1248-1253, the disclosure of which is incorporated by reference in its entirety. For example, 200 mL of water and 1 mL of 15.8 N nitric acid can be charged to a flask. Then, about 15.5 g of Al(NO$_3$)$_3$.9H$_2$O and about 5.5 g of (NH$_4$)$_2$HPO$_4$ is added to the flask and dissolved. Ammonia is then added until a pH of about 8.7 is reached. After stirring for 1 hr, vacuum filtering, and washing with water, the catalyst is dried at 120° C. for 12-16 hr, and calcined at 500° C. in air for 30 min Constructive Example 16 can be conducted in substantially the same manner as Example 10, with the LZY-54 catalyst replaced by the aluminum phosphate. Constructive Example 17 can be conducted in substantially the same manner as Example 11, with the LZY-54 catalyst replaced by the aluminum phosphate.

Constructive Examples 18-19

Constructive synthesis of 2,5-dimethylpyrrole from 2,5-dimethylfuran using a base-functionalized aluminum phosphate catalyst The base-functionalized aluminum phosphate catalyst can be produced as disclosed in *Top. Catal.*, (2010) 53, 1248-

1253, the disclosure of which is incorporated by reference in its entirety. After producing aluminum phosphate as described in Constructive Examples 16-17, the aluminum phosphate is placed in a tube furnace and purged with $N_2$, then flowing 240 mL/min $NH_3$ along with 230 mL/min $N_2$ for 16 hr at about 800° C. The resultant material is placed in an oven under vacuum at 150° C. overnight to remove physisorbed ammonia.

Constructive Example 18 can be conducted in substantially the same manner as Example 10, with the LZY-54 catalyst replaced by the base-functionalized aluminum phosphate. Constructive Example 19 can be conducted in substantially the same manner as Example 11, with the LZY-54 catalyst replaced by the base-functionalized aluminum phosphate.

Constructive Examples 20-21

Constructive synthesis of 2,5-dimethylpyrrole from 2,5-dimethylfuran using a base-functionalized aluminum phosphate catalyst The base-functionalized aluminum phosphate catalyst can be produced as disclosed in *Top. Catal.*, (2010) 53, 1248-1253, the disclosure of which is incorporated by reference in its entirety. After producing aluminum phosphate as described in Constructive Examples 16-17, the aluminum phosphate is placed in a tube furnace and purged with $N_2$, then flowing 240 mL/min $NH_3$ along with 230 mL/min $N_2$ for 72 hr at about 800° C. The resultant material is placed in an oven under vacuum at 150° C. overnight to remove physisorbed ammonia.

Constructive Example 20 can be conducted in substantially the same manner as Example 10, with the LZY-54 catalyst replaced by the base-functionalized aluminum phosphate. Constructive Example 21 can be conducted in substantially the same manner as Example 11, with the LZY-54 catalyst replaced by the base-functionalized aluminum phosphate.

Constructive Examples 22-23

Constructive synthesis of 2,5-dimethylpyrrole from 2,5-dimethylfuran using a SBA-15 mesoporous silica catalyst The SBA-15 mesoporous silica catalyst can be produced as disclosed in *J. Cat.*, (2009) 263, 181-188, the disclosure of which is incorporated by reference in its entirety. For example, about 4 g of Pluronic P123 is dissolved in a mixture of 125 mL water and 25 mL HCl (~12 N). Tetraethyl orthosilicate (TEOS) is added as a silica precursor at 40° C. at a molar ratio of 1 TEOS:7.76 HCl:171 $H_2O$. The resultant mixture is stirred at 40° C. for 20 hr and aged at 90° C. for 24 hr before being filtered. After filtering and washing with ethanol, excess protons from the acidic synthesis conditions are removed with a 5 mL tetramethylammonium hydroxide (TMAH) solution (25 wt % in methanol) in 45 mL methanol while stirring for 30 min. The catalyst can be dried at 100° C. for 4-8 hr under vacuum.

Constructive Example 22 can be conducted in substantially the same manner as Example 10, with the LZY-54 catalyst replaced by the SBA-15 mesoporous silica. Constructive Example 23 can be conducted in substantially the same manner as Example 11, with the LZY-54 catalyst replaced by the SBA-15 mesoporous silica.

Constructive Examples 24-25

Constructive synthesis of 2,5-dimethylpyrrole from 2,5-dimethylfuran using an aminopropyl-functionalized SBA-15 mesoporous silica catalyst The aminopropyl-functionalized SBA-15 mesoporous silica catalyst can be produced as disclosed in *J. Cat.*, (2009) 263, 181-188, the disclosure of which is incorporated by reference in its entirety. For example, about 4 g of Pluronic P123 is dissolved in a mixture of 125 mL water and 25 mL HCl (~12 N). Tetraethyl orthosilicate (TEOS) is added as a silica precursor at 40° C. The 3-aminopropyltri-ethoxysilane (APTES) is added after a TEOS pre-hydrolysis period of about 1 hr. The resulting mixture (1 TEOS:0.1 APTES:7.76 HCl:171 $H_2O$ molar ratio) is stirred at 40° C. for 20 hr and aged at 90° C. for 24 hr before being filtered. The surfactant template can be removed by refluxing in ethanol with 10 wt % HCl for 24 hr. The resultant material is then filtered and washed with ethanol. Excess protons from the acidic synthesis conditions are removed with a 5 mL tetramethylammonium hydroxide (TMAH) solution (25 wt % in methanol) in 45 mL methanol while stirring for 30 min. The catalyst can be dried at 100° C. for 4-8 hr under vacuum.

Constructive Example 24 can be conducted in substantially the same manner as Example 10, with the LZY-54 catalyst replaced by the aminopropyl-functionalized SBA-15 mesoporous silica. Constructive Example 25 can be conducted in substantially the same manner as Example 11, with the LZY-54 catalyst replaced by the aminopropyl-functionalized SBA-15 mesoporous silica.

Constructive Examples 26-27

Constructive synthesis of 2,5-dimethylpyrrole from 2,5-dimethylfuran using a silylated aminopropyl-functionalized SBA-15 mesoporous silica catalyst The silylated aminopropyl-functionalized SBA-15 mesoporous silica catalyst can be produced as disclosed in *J. Cat.*, (2009) 263, 181-188, the disclosure of which is incorporated by reference in its entirety. A suspension of aminopropyl-functionalized SBA-15 mesoporous silica catalyst, as described in Constructive Examples 24-25, in toluene is combined with 5 mL of 1,1,1,3,3,3,-hexamethyldisilazane (HMDS) diluted in 5 mL of toluene. The resultant mixture is refluxed for 24 hr, then filtered and washed with toluene and ethanol. The catalyst can be dried at 100° C. for 4-8 hr under vacuum.

Constructive Example 26 can be conducted in substantially the same manner as Example 10, with the LZY-54 catalyst replaced by the silylated aminopropyl-functionalized SBA-15 mesoporous silica. Constructive Example 27 can be conducted in substantially the same manner as Example 11, with the LZY-54 catalyst replaced by the silylated aminopropyl-functionalized SBA-15 mesoporous silica.

Constructive Examples 28-29

Constructive synthesis of 2,5-dimethylpyrrole from 2,5-dimethylfuran using a propylsulfonic acid-functionalized SBA-15 mesoporous silica catalyst The propylsulfonic acid-functionalized SBA-15 mesoporous silica catalyst can be produced as disclosed in *Appl.*

*Catal. A: Gen.*, (2009) 359, 113-120, the disclosure of which is incorporated by reference in its entirety. For example, about 4 g of Pluronic P123 (tri-block copolymer of polyethylene oxide-polypropylene oxide-polyethylene oxide with the molecular structure $PEO_{20}$-$PPO_{70}$-$PEO_{20}$) is dissolved in 125 g of 1.9 M HCl at room temperature while stirring, with subsequent heating to 40° C. before adding tetraethoxysilane (TEOS). Approximately 45 min can be allowed for prehydrolysis of TEOS prior to the addition of a (3-mercaptopropyl)trimethoxysilane (MPTMS)-$H_2O_2$ solution. The resulting mixture, with a molar composition of about 0.037 TEOS, 0.004 MPTMS, and 0.037 $H_2O_2$ is stirred for 24 hr at 40° C. and thereafter can be aged for 24 hr at 100° C. under static conditions. The product can be collected and subjected to extraction by refluxing in ethanol three times. The amount of sulfonic acid group loading can depend on the amount of MPTMS employed. This product is vacuum dried at 100° C. for about 4-8 hr.

Then, about 2 grams of the dried product is suspended in a mixture of about 0.004 mol of propyltrimethoxysilane (PrTMS) in 200 mL toluene and refluxed for 4 hr. The resultant product is collected by washing with toluene. The final catalyst is vacuum dried at 100° C. for 4-8 hr.

Constructive Example 28 can be conducted in substantially the same manner as Example 10, with the LZY-54 catalyst replaced by the propylsulfonic acid-functionalized SBA-15 mesoporous silica. Constructive Example 29 can be conducted in substantially the same manner as Example 11, with the LZY-54 catalyst replaced by the propylsulfonic acid-functionalized SBA-15 mesoporous silica.

We claim:

1. A process for producing a substituted pyrrole compound, the process comprising:
   1) contacting
      a) a substituted furan compound;
      b) ammonia, an ammonium salt, or a combination thereof; and
      c) a catalyst comprising an acidic resin; and
   2) forming the substituted pyrrole compound.

2. The process of claim 1, wherein the substituted pyrrole compound is a compound of the formula:

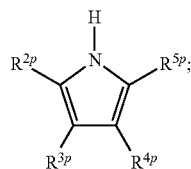

P1 wherein:
$R^{2p}$, $R^{3p}$, $R^{4p}$, and $R^{5p}$ independently are a hydrogen atom, a $C_1$-$C_{30}$ organyl group, or a $C_3$-$C_{60}$ silyl group, and at least one of $R^{2p}$, $R^{3p}$, $R^{4p}$, and $R^{5p}$ is not a hydrogen atom.

3. The process of claim 2, wherein $R^{2p}$, $R^{3p}$, $R^{4p}$, and $R^{5p}$ independently are a hydrogen atom or a $C_1$-$C_{18}$ hydrocarbyl group, and at least one of $R^{2p}$, $R^{3p}$, $R^{4p}$, and $R^{5p}$ is not a hydrogen atom.

4. The process of claim 2, wherein $R^{2p}$ and $R^{5p}$ independently are a $C_1$-$C_{18}$ hydrocarbyl group, and $R^{3p}$ and $R^{4p}$ are hydrogen.

5. The process of claim 2, wherein $R^{2p}$ and $R^{5p}$ independently are a methyl group, an ethyl group, an n-propyl group, an iso-propyl group, an n-butyl group, a t-butyl group, a phenyl group, a benzyl group, a tolyl group, or a xylyl group.

6. The process of claim 2, wherein at least one of $R^{2p}$ and $R^{5p}$ is a hydrogen atom.

7. The process of claim 1, wherein the substituted pyrrole compound comprises a compound of formula P2, P3, P4 or P5:

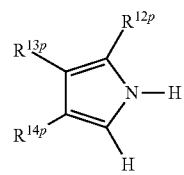

P2

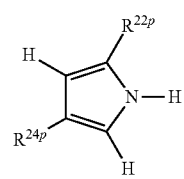

P3

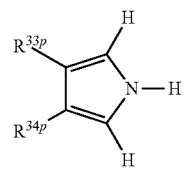

P4

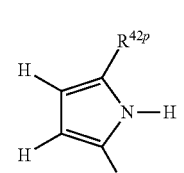

P5 wherein $R^{12p}$, $R^{13p}$, $R^{14p}$, $R^{22p}$, $R^{24p}$, $R^{33p}$, $R^{34}$, $R^{42}$, and $R^{45}$ independently are a $C_1$-$C_{18}$ hydrocarbyl group.

8. The process of claim 1, wherein the substituted pyrrole compound comprises 2,5-dimethylpyrrole, 2-methyl-5-ethylpyrrole, 2,5-diethylpyrrrole, 2-ethyl-5-methylpyrrole, 2-ethyl-5-n-propylpyrrole, 2,5-di-n-propylpyrrole, 2,5-diisopropylpyrrole, 2,5-di-n-butylpyrrole, 2,5-di-n-pentylpyrrole, 2,5-di-n-hexylpyrrole, 2,5-di-n-heptylpyrrole, 2,5-di-n-octylpyrrole, 2,3,5-triethylpyrrrole, 2,3,5-tri-n-butylpyrrole, 2,3,5-tri-n-pentylpyrrole, 2,3,5-tri-n-hexylpyrrole, 2,3,5-tri-n-heptylpyrrole, 2,3,5-tri-n-octylpyrrole, 2,3,4,5-tetraethylpyrrole, 2,3,4,5-tetra-n-butylpyrrole, 2,3,4,5-tetra-n-hexylpyrrole, 2,5-dibenzylpyrrole, 2,4-dimethylpyrrole, 2-methyl-4-isopropylpyrrole, 2,4-dimethyl-3-ethylpyrrole, 2,4-diethylpyrrole, 2-ethyl-4-isopropylpyrrole, 2-methyl-4-sec-butylpyrrole, 2-ethyl-4-sec-butylpyrrole, 2-methyl-4-isobutylpyrrole, 2-ethyl-4-isobutylpyrrole, 2-methyl-4-t-butylpyrrole, 2-ethyl-4-t-butylpyrrole, 2-methyl-4-neopentylpyrrole, 2-ethyl-4-neopentylpyrrole, 3,4-dimethylpyrrole, 3,4-diethylpyrrole, 3,4-diisopropylpyrrole, 3,4-di-sec-butylpyrrole, 3,4-diisobutylpyrrole, 3,4-di-t-butylpyrrole, 3,4-di-neopentylpyrrole, or any combination thereof.

9. The process of claim 1, wherein the substituted pyrrole compound comprises 2,5-dimethylpyrrole.

10. The process of claim 1, wherein ammonia is contacted with the substituted furan compound and the catalyst.

11. The process of claim 1, wherein the ammonium salt is contacted with the substituted furan compound and the catalyst, and wherein the ammonium salt comprises ammonium acetate, ammonium carbonate, ammonium bicarbonate, ammonium chloride, ammonium hydroxide, ammonium nitrate, ammonium phosphate, ammonium sulfate, or any combination thereof.

12. The process of claim 1, wherein the acidic resin comprises an AMBERLYST® catalyst resin, a NAFION® catalyst resin, or a combination thereof.

13. The process of claim 1, wherein an equivalent ratio of the ammonia, the ammonium salt, or a combination thereof, to the substituted furan compound is in a range from 0.975:1 to 50:1.

14. The process of claim 1, wherein the substituted pyrrole compound is formed:
   at a pressure in a range from 25 psig to 3500 psig;
   at a temperature in a range from 50° C. to 400° C.;
   at a weight hourly space velocity in a range from 0.05 to 50;
   in the presence of added water;
   in the presence of an organic solvent;
   in a continuous reactor; or
   any combination thereof.

15. The process of claim 1, wherein the substituted pyrrole compound is formed:
   in the substantial absence of added water;
   in the presence of a water scavenger; or
   both.

16. The process of claim 1, wherein step 1 and step 2 are conducted in a single reactor.

17. The process of claim 1, wherein the acidic resin comprises a styrene-divinylbenzene resin, a 4-vinylpyridine divinylbenzene resin, an ionomer resin, a tetrafluoroethylene resin modified with perfluorovinyl ether groups terminated with sulfonate groups, or any combination thereof.

18. A process for producing a substituted pyrrole compound, the process comprising:
   1) contacting
      a) a substituted furan compound;
      b) ammonia, an ammonium salt, or a combination thereof; and
      c) a catalyst comprising a treated solid oxide; and
   2) forming the substituted pyrrole compound;
   wherein the treated solid oxide comprises fluorided alumina, chlorided alumina, bromided alumina, fluorided silica-alumina, chlorided silica-alumina, bromided silica-alumina, fluorided silica-zirconia, chlorided silica-zirconia, bromided silica-zirconia, fluorided silica-titania, fluorided silica-coated alumina, or any combination thereof.

19. The process of claim 18, wherein the substituted pyrrole compound is a compound of the formula:

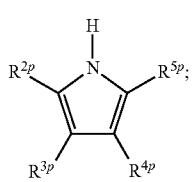

P1 wherein $R^{2p}$ and $R^{5p}$ independently are a $C_1$-$C_{18}$ hydrocarbyl group, and $R^{3p}$ and $R^{4p}$ are hydrogen.

20. The process of claim 18, wherein the substituted pyrrole compound comprises a compound of formula P2, P3, P4 or P5:

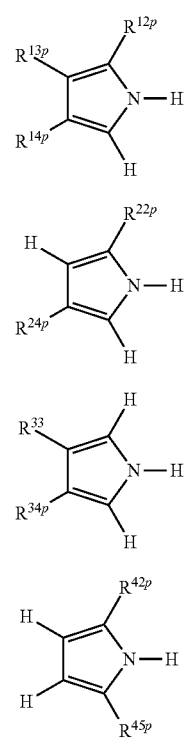

wherein $R^{12p}$, $R^{13p}$, $R^{14p}$, $R^{22p}$, $R^{24p}$, $R^{33p}$, $R^{34}$, $R^{42}$, and $R^{45}$ independently are a $C_1$-$C_{18}$ hydrocarbyl group.

21. The process of claim 18, wherein the substituted pyrrole compound is formed:
   at a pressure in a range from 25 psig to 3500 psig;
   at a temperature in a range from 50° C. to 400° C.;
   at a weight hourly space velocity in a range from 0.05 to 50;
   in the presence of added water;
   in the presence of an organic solvent;
   in a continuous reactor; or
   any combination thereof.

22. The process of claim 21, wherein the substituted pyrrole compound comprises 2,5-dimethylpyrrole.

23. A process for producing a substituted pyrrole compound, the process comprising:
   1) contacting
      a) a substituted furan compound;
      b) ammonia, an ammonium salt, or a combination thereof and
      c) a catalyst comprising a halided solid oxide; and
   2) forming the substituted pyrrole compound.

* * * * *

UNITED STATES PATENT AND TRADEMARK OFFICE
CERTIFICATE OF CORRECTION

PATENT NO. : 8,362,278 B2
APPLICATION NO. : 12/895945
DATED : January 29, 2013
INVENTOR(S) : Bruce E. Kreischer et al.

It is certified that error appears in the above-identified patent and that said Letters Patent is hereby corrected as shown below:

In the claims:

Column 46, line 40: "$R^{34}$, $R^{42}$" should be changed to --$R^{34p}$, $R^{42p}$--.
Column 46, line 41: "$R^{45}$" should be changed to --$R^{45p}$--.

Column 48, line 38: "$R^{34}$, $R^{42}$" should be changed to --$R^{34p}$, $R^{42p}$--.
Column 48, line 39: "$R^{45}$" should be changed to --$R^{45p}$--.

Signed and Sealed this
Fourth Day of November, 2014

Michelle K. Lee
*Deputy Director of the United States Patent and Trademark Office*